United States Patent
Liu et al.

(10) Patent No.: US 12,109,237 B2
(45) Date of Patent: Oct. 8, 2024

(54) S309 CHIMERIC ANTIGEN RECEPTORS AND METHODS OF USE

(71) Applicant: Rutgers, The State University of New Jersey, New Brunswick, NJ (US)

(72) Inventors: Dongfang Liu, Millburn, NJ (US); Minh Ma, New Brunswick, NJ (US); Saiaditya Badeti, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 232 days.

(21) Appl. No.: 17/551,006

(22) Filed: Dec. 14, 2021

(65) Prior Publication Data

US 2022/0184125 A1     Jun. 16, 2022

Related U.S. Application Data

(60) Provisional application No. 63/125,820, filed on Dec. 15, 2020.

(51) Int. Cl.
| | |
|---|---|
| *A61K 35/17* | (2015.01) |
| *A61P 31/14* | (2006.01) |
| *C07K 14/54* | (2006.01) |
| *C07K 14/705* | (2006.01) |
| *C07K 14/715* | (2006.01) |
| *C07K 14/725* | (2006.01) |
| *C07K 16/10* | (2006.01) |
| *A61K 38/00* | (2006.01) |
| *A61K 39/00* | (2006.01) |

(52) U.S. Cl.
CPC .............. *A61K 35/17* (2013.01); *A61P 31/14* (2018.01); *C07K 14/5443* (2013.01); *C07K 14/7051* (2013.01); *C07K 14/70521* (2013.01); *C07K 14/7151* (2013.01); *C07K 16/10* (2013.01); *A61K 38/00* (2013.01); *A61K 39/00* (2013.01); *C07K 2317/565* (2013.01); *C07K 2317/622* (2013.01)

(58) Field of Classification Search
CPC ............................ A61K 35/17; C07K 14/5443
See application file for complete search history.

(56) References Cited

U.S. PATENT DOCUMENTS

2021/0261650 A1* 8/2021 Corti et al. ............ C07K 16/10

OTHER PUBLICATIONS

Mancini et al. (Adoptive T-cell therapy in the treatment of viral and opportunistic fungal infections. Future Microbiology, 10(4), 665-682 (2015). (Year: 2015).*
Hurton et al. (Tethered IL-15 augments antitumor activity and promotes a stem-cell memory subset in tumor-specific T cells. Proceedings of the National Academy of Sciences of the United States of America, 113(48), E7788-E7797 (2016). (Year: 2016).*
Tortorici et al. (Ultrapotent human antibodies protect against SARS-CoV-2 challenge via multiple mechanisms. Science 370,950-957(2020). (Year: 2020).*
Liu et al., "Chimeric antigen receptor (CAR)-modified natural killer cell-based immunotherapy and immunological synapse formation in cancer and HIV," *Protein Cell*, vol. 8, No. 12, pp. 861-877, 2017.
Ma et al., "Efficacy of Targeting SARS-CoV-2 by CAR-NK Cells," *bioRxiv*, https://doi.org/10.1101/2020.08.11.247320, Aug. 12, 2020 (34 pages).
Pinto et al., "Cross-neutralization of SARS-CoV-2 by a human monoclonal SARS-CoV antibody," *Nature*, vol. 583, pp. 290-295, 2020 (including supplemental materials).
Soleimanian and Yaghobi, "Harnessing Memory NK Cell to Protect Against COVID-19," *Frontiers in Pharmacology*, vol. 11, Article 1309, 2020 (14 pages).

* cited by examiner

*Primary Examiner* — Daniel E Kolker
*Assistant Examiner* — Estella M. Gustilo
(74) *Attorney, Agent, or Firm* — Klarquist Sparkman, LLP

(57) ABSTRACT

Chimeric antigen receptors (CARs) including an scFv binding to coronavirus spike protein (S309 scFv), nucleic acids encoding the CARs, vectors including nucleic acids encoding the CARs, and cells expressing the CARs are provided. Methods of treating a subject with coronavirus are also provided, including administering to the subject a modified immune cell expressing a disclosed CAR.

16 Claims, 18 Drawing Sheets

Specification includes a Sequence Listing.

FIG. 2D

Pseudotyped SARS-CoV-2 S | Full-length S recombinant protein | S1 subunit recombinant protein Binding efficiency (%)

****

NK92MI: —
293T-hACE2: 74.7333
S309-CAR-NK92MI: 90.8333, 88.4333, 95.8667

S309 CHIMERIC ANTIGEN RECEPTORS AND METHODS OF USE

CROSS REFERENCE TO RELATED APPLICATION

This claims the benefit of U.S. Provisional Application No. 63/125,820, filed Dec. 15, 2020, which is incorporated herein by reference in its entirety.

ACKNOWLEDGMENT OF GOVERNMENT SUPPORT

This invention was made with government support under grant number AI130197 awarded by the National Institutes of Health. The government has certain rights in the invention.

FIELD

This disclosure relates to chimeric antigen receptors, particular chimeric antigen receptors targeting coronavirus spike protein, and methods of their use for treating coronavirus infection.

BACKGROUND

Severe Acute Respiratory Syndrome Coronavirus 2 (SARS-CoV-2) is highly contagious, and is now widespread throughout the world. The disease caused by SARS-CoV-2 (COVID-19) presents severe symptoms including pneumonia, acute respiratory distress syndrome, neurological symptoms, organ failure, and death. More importantly, severe COVID-19 patients may experience dysregulation of an appropriate immune response, characterized by lymphopenia, high neutrophil levels, and increased pro-inflammatory cytokines and chemokines (Song et al., *Nat. Commun.* 11:3410, 2020).

Current treatments for COVID-19 patients can be classified into three categories: anti-viral treatments, immunosuppression-based treatments, and other supporting treatments such as convalescent plasma. Specifically, in a few trials patients have been given combinations of antivirals including umifenovir (Xu et a., *Mil. Med. Res.* 7:22, 2020), remdesivir/ribavirin (Jean et al., *J. Microbiol. Immunol. Infect.* 53:436-443, 2020), chloroquine (Shah et al., *Int. J. Rheum. Dis.* 23:613-619, 2020), the chloroquine analog hydroxychloroquine (Chowdhury et al., *Acad. Emerg. Med.* 27:493-504, 2020), and/or lopinavir/ritonavir (Dong et al., *Drug Discov. Ther.* 15:58-60, 2020; Russell et al., *Ecancermedicalscience* 14:1022, 2020). Non-steroidal anti-inflammatory drugs (NSAIDs), antibodies against IL-6 receptors, and corticosteroids have also been used during the early acute phase of SARS-CoV-2 to suppress the overactivated immune response (Dong et al., *Drug Discov. Ther.* 15:58-60, 2020). Other supporting therapies including supplemental oxygen and mechanical ventilatory support have also been used when indicated (e.g., intubation, etc.).

Natural killer (NK) cells have been shown to participate in the first line of defense in humans and mice against pathogen-infected or malignant cells. There are three known defense mechanisms by which NK cells use to mediate killing: production of cytokines such as IFN-γ to stimulate other direct antiviral mechanisms, release of lytic granules, (stored effector molecules such as perforin and granzymes) by direct binding through stimulatory receptors, and induction of apoptosis through the interaction of TNF-related apoptosis induction ligand (TRAIL) on NK cells to the death receptors on the target cells.

Clinically, natural killer (NK) cells were first defined as $CD56^{bright}CD16^-$ and $CD56^{dim}CD16^{+\ cells}$ in the peripheral blood. NK cells isolated from peripheral blood can be further modified to express chimeric antigen receptors (CARs) for treating a variety of cancers and infectious diseases (Liu et al., *Protein Cell* 8:861-877, 2017). Recent preclinical studies of CAR-NK cells in cancer immunotherapy show several advantages over CAR-T cells in clinical safety. Unlike CAR-T, CAR-NK cells do not present additional risk for the development of severe graft-versus-host-disease (GVHD). More importantly, CAR-NK cells are associated with reduced host cytotoxicity compared to CAR-T cells. In particular, NK cells are less likely to induce cytokine release syndrome (CRS) that could potentially exacerbate COVID-19 symptoms in severe patients (Shah et al., *Br. J. Haematol.* 177:457-466, 2017).

SUMMARY

Previous studies show that the genome sequence of SARS-CoV-2 is 77% identical to that of SARS-CoV (Zhou et al., *Nature* 579:270-273, 2020). Several neutralizing antibodies were isolated from memory B cells of convalescent SARS patients. One of these, named S309, potently neutralizes both pseudotyped SARS-CoV-2 viral particles and authentic SARS-CoV-2 by binding to both the 'closed' and 'open' ectodomain trimer conformations of the SARS-CoV-2 Spike glycoprotein (Pinto et al., *Nature* 583:290-295, 2020).

Provided herein is a novel approach for the generation of CAR-NK cells for targeting SARS-CoV-2 using the scFv domain of S309. Compared to previously generated Spike protein-targeting CAR-NK cells, S309-CAR-NK cells show superior killing activities against pseudotyped SARS-CoV-2 virus. This demonstrates that 'off-the-shelf' S309-CAR-NK cells may have the potential to prevent SARS-CoV-2 infection, as well as to treat immunocompromised patients or those with comorbidities such as diabetes, malnutrition, and certain genetic disorders.

In some embodiments, disclosed is a chimeric antigen receptor including an antigen binding domain that specifically binds coronavirus spike protein, such as an scFv of antibody S309; a hinge domain; a transmembrane domain; and an intracellular domain. In some embodiments, the antigen binding domain includes the variable heavy chain (VH) domain complementarity determining region 1 (CDR1), CDR2 and CDR3 amino acid sequences of amino acid positions 47-54, 72-79, and 118-137 of SEQ ID NO: 1, respectively, and the variable light chain (VL) domain CDR1, CDR2 and CDR3 amino acid sequences of amino acid positions 195-201, 219-221, and 258-265 of SEQ ID NO: 1, respectively. In some examples, the antigen binding domain has at least 90% sequence identity amino acids 22-275 of SEQ ID NO: 1, or includes or consists of amino acids 22-275 of SEQ ID NO: 1. In some examples, the hinge domain comprises an IgG1 domain, the transmembrane domain comprises a CD28 transmembrane domain, and the intracellular domain comprises a CD28 domain, a 4-1BB domain, and a CD3ζ domain. In additional examples, the chimeric antigen receptor further includes an interleukin-15 (IL-15) domain. In non-limiting examples, the chimeric antigen receptor has at least 90% sequence identity to the amino acid sequence SEQ ID NO: 1 or SEQ ID NO: 4, or includes or consists of the amino acid sequence of SEQ ID NO: 1 or SEQ ID NO: 4.

Also provided are nucleic acids encoding the chimeric antigen receptors disclosed herein. In some embodiments, the antigen binding domain is encoded by a nucleic acid including the variable heavy chain (VH) domain complementarity determining region 1 (CDR1), CDR2 and CDR3 nucleic acid sequences of nucleic acid positions 139-162, 514-237, and 352-411 of SEQ ID NO: 5, respectively, and the variable light chain (VL) domain CDR1, CDR2 and CDR3 nucleic acid sequences of nucleic acid positions 583-603, 655-663, and 772-765 of SEQ ID NO: 5, respectively. In some embodiments, the nucleic acid encoding the S309 scFv is codon-optimized. In particular examples, the nucleic acid encoding the CAR has at least 90% sequence identity to the nucleic acid sequence of SEQ ID NO: 5 or SEQ ID NO: 8, or comprises or consists of the amino acid sequence of SEQ ID NO: 5 or SEQ ID NO: 8. The nucleic acids are included in a vector (such as a retroviral vector) in some embodiments.

Modified immune cells, for example, natural killer (NK) cells or T cells expressing the disclosed chimeric antigen receptor are provided. In some embodiments, the modified NK cell is an NK-92 cell or NK-92MI cell.

Also provided are methods of treating a subject having or suspected of having a coronavirus infection, including administering an effective amount of a modified NK cell expressing a disclosed CAR to the subject. In particular examples, the subject is infected with SARS-CoV-1 or SARS-CoV-2.

The foregoing and other features of the disclosure will become more apparent from the following detailed description, which proceeds with reference to the accompanying figures.

BRIEF DESCRIPTION OF THE DRAWINGS

FIG. 1A is a schematic diagram of an exemplary plasmid construct of a S309-CAR. The SFG retroviral vector contains the S309 single chain antibody fragment (PDB accession code 6WS6), a human IgG1 CH2CH3 hinge region, a CD28 transmembrane region, followed by the co-stimulatory CD28 and 4-1BB domains, and the intracellular domain of CD3ζ. FIG. 1B shows determination of S309-CAR-NK expression by flow cytometry. S309-CAR cells were collected and stained with anti-CD56 and CAR F(ab)2 domain [IgG (H+L)] for flow cytometry. The cells were then sorted to achieve a homogenous population of high CAR expression. FIG. 1C illustrates immunoprofiling of S309-CAR-NK by flow cytometry. S309-CAR and the wildtype NK-92MI cells were stained with antibodies against different immunomodulatory receptors including CTLA4, PD1, NKG2A, NKG2C, NKG2D, NKp46, CD56, CD16, 2B4, DNAM-1, CD94, KLRG1, TIM3, LAG3, and TIGIT.

FIGS. 2A-2D illustrate that S309-CAR-NK-92MI cells bind to RBD domain of SARS-CoV-2 S protein and pseudotyped SARS-CoV-2 viral particles. FIG. 2A is representative dot plots showing the efficiency of S309-CAR binding to SARS-CoV-2-RBD. S309-CAR or NK-92MI cells were incubated with the RBD recombinant protein of SARS-CoV-1 (left) or SARS-CoV-2 (right). FIG. 2B is a schematic diagram illustrating generation of pseudotyped SARS-CoV-2 viral particles. 293T cells were transfected with the indicated plasmids for 72 hours for the generation of pseudotyped SARS-CoV-2 viral particles. FIG. 2C shows representative histograms showing S309-CAR-NK binds to the pseudotyped SARS-CoV-2 viral particles. S309-CAR-NK or NK-92MI or 293T-hACE2 cells were incubated with pseudotyped SARS-CoV-2 viral particles, S1 subunit, or full-length S recombinant protein at 37° C. for 1 hour. Cells were then harvested and stained with anti-S1 subunit and evaluated by flow cytometry. The experimental sample was performed in triplicates with MFI=13579±251 (a.u.). FIG. 2D shows quantitative data of the binding efficiency of S309-CAR-NK to pseudotyped SARS-CoV-2 viral particles. The experimental sample was performed in triplicates with binding efficiency of over 90%. Data represent mean±standard error of the mean (SEM) of three independent experiments. Unpaired Student's t test was employed. ****p<0.0001.

FIG. 3A is a schematic diagram showing generation of transient 293T-hACE2-RBD and stable A549-Spike cell lines. 293T-hACE2 cells were transfected with RBD-containing plasmid for 48 hours. Transfected 293T-hACE2-RBD cells were then harvested. For the generation of A549-Spike, 293T cells were transfected with the retrovirus transfection system for 48 hours. The spike retrovirus was filtered and transduced into A549 cells for an additional 48-72 hours. FIG. 3B shows representative dot plots showing the expression of RBD or Spike in 293T-hACE2 (top) or A549 cell (bottom). 293T-hACE2-RBD and A549-Spike cells were stained with anti-RBD and the expression was confirmed by flow cytometry. The stable A549-Spike cell line was then sorted to achieve high levels of spike expression. FIG. 3C shows quantitative data of CD107a surface expression assay of S309-CAR-NK against 293T-hACE2-RBD or A549-Spike cell lines. Briefly, S309-CAR-NK-92MI cells were cocultured with either 293T-hACE2-RBD cells, A549-Spike cells, stimulated with PMA/Ionomycin, or incubated alone for 2 hours at 37° C. Cells were then harvested and stained for CAR F(ab)2 domain [IgG (H+L)] and CD107a. Data represent mean±SEM from two experiments. FIG. 3D shows a 4-hour gold standard $Cr^{51}$ release assay of S309-CAR-NK and NK-92MI against various target cell lines. 293T-hACE2-RBD (top), A549-Spike (middle), and HepG2 (bottom) cell lines were used as target cells for S309-CAR-NK and NK-92MI. Experimental groups were performed in triplicates. Error bars represent mean±SEM from at least two independent experiments. Unpaired Student's t test was used for both panels FIG. 3C and FIG. 3D. ns p>0.05, * p<0.05,  p<0.01, * p<0.001, and **** p<0.0001.

FIG. 4A is a schematic representation of human primary S309-CAR-NK expansion system. Briefly, irradiated (100 Gy) 221-mIL21 feeder cells were cocultured with PBMC supplemented with IL-2 and IL-15 on Day 0. In parallel, 293T cells were transfected with the retrovirus packaging system to produce S309-CAR retrovirus that were then transduced into the expanded PBNK cells in the presence of IL-2 and IL-15. Primary S309-CAR-NK cells were harvested on Day 7 and continued expansion for 21 days. FIG. 4B shows representative dot plots of expanded primary NK cells and primary S309-CAR-NK. The purity of NK cells and the expression of CAR were monitored every 3-4 days. FIG. 4C shows immunophenotyping of primary S309-CAR-NK cells using flow cytometry. Antibodies against various immunomodulatory receptors including CTLA4, PD1, NKG2A, CD56, CD16, 2B4, NKG2C, NKG2D, NKp46, DNAM-1, CD94, TIGIT, KLRG1, TIM3, and LAG3 were used to stain both primary NK cells and S309-CAR-NK. FIG. 4D is a graph showing quantitative data of cytotoxic activity of primary S309-CAR-NK against A549-Spike. Briefly, expanded S309-CAR-NK cells were blocked with anti-CD16 for 30 minutes and then anti-NKG2D for 30 minutes on ice. The target cells were labeled with $Cr^{51}$ for 2 hours prior to coculturing with primary S309-CAR-NK cells for an additional 4 hours. The experiment was repeated at least twice. Error bars represent SEM. Unpaired Student's t test was used.  p<0.01, * p<0.001, and **** p<0.0001.

FIG. 5A is a diagram of S309 and CR3022 neutralizing antibodies binding to different epitopes of the SARS-CoV-2 S protein. Both open and closed conformation states of SARS-CoV-2 S protein are shown. FIG. 5B shows quantitative data of CD107a surface expression of both S309-CAR-NK-92MI and CR3022-CAR-NK-92MI. Both transient 293T-hACE2-RBD and stable A549-Spike cell lines were used as target cells. Error bars represent SEM from at least two independent experiments. FIG. 5C shows a comparison of killing activity of S309-CAR and CR3022-CAR using the 4-hour $Cr^{51}$ release assay. Effector cells were cocultured with $Cr^{51}$-labeled target cells at 37° C. for 4 hours. The assay was repeated for at least two times per target cell line. FIG. 5D shows that expanded primary S309-CAR-NK cells have increased killing activity against A549-Spike cells compared to primary CR3022-CAR-NK. Effector cells were blocked with anti-CD16 and anti-NKG2D prior to coculturing with A549-Spike target cells for 4 hours at 37° C. Data were pooled from three independent experiments. Unpaired Student's t test was employed for all panels. ns p>0.05, * p<0.05,  p<0.01, * p<0.001, and **** p<0.0001.

FIGS. 6A and 6B illustrate that primary S309-CAR-NK cells effectively bind to all existing variants of SARS-CoV-2 pseudotyped virus. FIG. 6A is a representative histogram showing the SARS-CoV-2 pseudovirus binding efficiency of primary S309-CAR-NK cells. FIG. 6B is a bar graph showing the SARS-CoV-2 pseudovirus binding efficiency of primary S309-CAR-NK cells. Primary un-transduced NK cells or S309-CAR-NK cells, or 293T-hACE2 cells were incubated with SARS-CoV-2 pseudotyped virus for 2 hours at 37° C. prior to staining with anti-spike and flow cytometry. Error bars represent±SEM. Experiment was repeated three times.

SEQUENCE LISTING

Figure 1A:
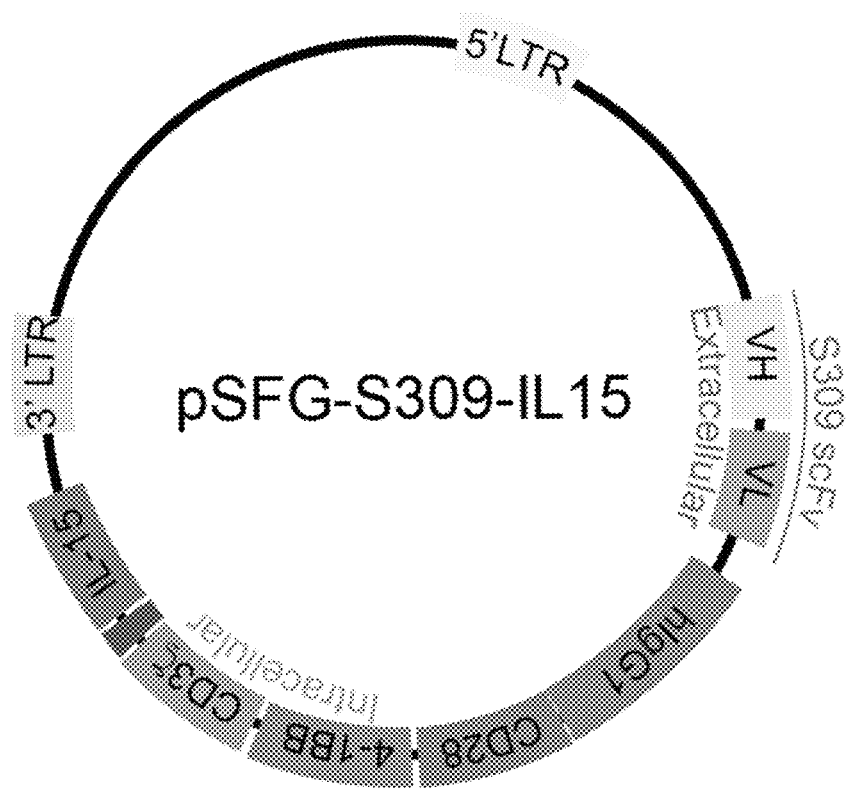
FIGS. 1A-1C show generation of S309-CAR-NK-92MI cells.

Any nucleic acid and amino acid sequences listed herein or in the accompanying Sequence Listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Dec. 14, 2021, and is 27,191 bytes, which is incorporated by reference herein.

SEQ ID NO: 1 is the amino acid sequence of an exemplary S309-CAR:

MEFGLSWLFLVAILKGVQCVDQVQLVQSGAEVKKPGASVKVSCKASGYPF
TSYGISWVRQAPGQGLEWMGWISTYNGNTNYAQKFQGRVTMTTDTSTTTG
YMELRRLRSDDTAVYYCARDYTRGAWFGESLIGGFDNWGQGTLVTVSSGG
GGSGGGGSGGGGSGGGGSEIVLTQSPGTLSLSPGERATLSCRASQTVSST
SLAWYQQKPGQAPRLLIYGASSRATGIPDRFSGSGSGTDFTLTISRLEPE
DFAVYYCQQHDTSLTFGGGTKVEIKSYVTVSSQDPAEPKSPDKTHTCPPC
PAPELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALP
APIEKTISKAKGQPREPQVYTLPPSRDELTKNQVSLTCLVKGFYPSDIAV
EWESNGQPENNYKTTPPVLDSDGSFFLYSKLTVDKSRWQQGNVFSCSVMH
EALHNHYTQKSLSLSPGKKDPKFWVLVVVGGVLACYSLLVTVAFIIFWVR
SKRSRLLHSDYMNMTPRRPGPTRKHYQPYAPPRDFAAYRSKRGRKKLLYI
FKQPFMRPVQTTQEEDGCSCRFPEEEEGGCELRVKFSRSADAPAYQQGQN
QLYNELNLGRREEYDVLDKRRGRDPEMGGKPRRKNPQEGLYNELQKDKMA
EAYSEIGMKGERRRGKGHDGLYQGLSTATKDTYDALHMQALPPR

SEQ ID NO: 2 is the amino acid sequence of an exemplary E2A protein:

QCTNYALLKLAGDVESNPGP

SEQ ID NO: 3 is the amino acid sequence of an exemplary interleukin-15 protein:

MRISKPHLRSISIQCYLCLLLNSHFLTEAGIHVFILGCFSAGLPKTEANW
VNVISDLKKIEDLIQSMHIDATLYTESDVHPSCKVTAMKCFLLELQVISL
ESGDASIHDTVENLIILANNSLSSNGNVTESGCKECEELEEKNIKEFLQS
FVHIVQMFINTS

SEQ ID NO: 4 is the amino acid sequence of an exemplary S309-CAR-IL-15:

MEFGLSWLFLVAILKGVQCVDQVQLVQSGAEVKKPGASVKVSCKASGYPF
TSYGISWVRQAPGQGLEWMGWISTYNGNTNYAQKFQGRVTMTTDTSTTTG
YMELRRLRSDDTAVYYCARDYTRGAWFGESLIGGFDNWGQGTLVTVSSGG
GGSGGGGSGGGGSGGGGSEIVLTQSPGTLSLSPGERATLSCRASQTVSST
SLAWYQQKPGQAPRLLIYGASSRATGIPDRFSGSGSGTDFTLTISRLEPE
DFAVYYCQQHDTSLTFGGGTKVEIKSYVTVSSQDPAEPKSPDKTHTCPPC
PAPELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALP
APIEKTISKAKGQPREPQVYTLPPSRDELTKNQVSLTCLVKGFYPSDIAV
EWESNGQPENNYKTTPPVLDSDGSFFLYSKLTVDKSRWQQGNVFSCSVMH
EALHNHYTQKSLSLSPGKKDPKFWVLVVVGGVLACYSLLVTVAFIIFWVR
SKRSRLLHSDYMNMTPRRPGPTRKHYQPYAPPRDFAAYRSKRGRKKLLYI

FKQPFMRPVQTTQEEDGCSCRFPEEEEGGCELRVKFSRSADAPAYQQGQN

QLYNELNLGRREEYDVLDKRRGRDPEMGGKPRRKNPQEGLYNELQKDKMA

EAYSEIGMKGERRRGKGHDGLYQGLSTATKDTYDALHMQALPPRQCTNYA

LLKLAGDVESNPGPMRISKPHLRSISIQCYLCLLLNSHFLTEAGIHVFIL

GCFSAGLPKTEANWVNVISDLKKIEDLIQSMHIDATLYTESDVHPSCKVT

AMKCFLLELQVISLESGDASIHDTVENLIILANNSLSSNGNVTESGCKEC

EELEEKNIKEFLQSFVHIVQMFINTS

SEQ ID NO: 5 is a nucleic acid sequence encoding an exemplary S309-CAR:

ATGGAGTTTGGGCTGAGCTGGCTTTTTCTTGTGGCTATTTTAAAAGGTGT

CCAGTGCGTCGACCAGGTGCAGCTGGTGCAGAGCGGCGCGGAAGTGAAAA

AACCGGGCGCGAGCGTGAAAGTGAGCTGCAAAGCGAGCGGCTATCCGTTT

ACCAGCTATGGCATTAGCTGGGTGCGCCAGGCGCCGGGCCAGGGCCTGGA

ATGGATGGGCTGGATTAGCACCTATAACGGCAACACCAACTATGCGCAGA

AATTTCAGGGCCGCGTGACCATGACCACCGATACCAGCACCACCACCGGC

TATATGGAACTGCGCCGCCTGCGCAGCGATGATACCGCGGTGTATTATTG

CGCGCGCGATTATACCCGCGGCGCGTGGTTTGGCGAAAGCCTGATTGGCG

GCTTTGATAACTGGGGCCAGGGCACCCTGGTGACCGTGAGCAGCGGTGGT

GGTGGTTCTGGTGGTGGTGGTTCTGGCGGCGGCGGCTCCGGTGGTGGTGG

ATCCGAAATTGTGCTGACCCAGAGCCCGGGCACCCTGAGCCTGAGCCCGG

GCGAACGCGCGACCCTGAGCTGCCGCGCGAGCCAGACCGTGAGCAGCACC

AGCCTGGCGTGGTATCAGCAGAAACCGGGCCAGGCGCCGCGCCTGCTGAT

TTATGGCGCGAGCAGCCGCGCGACCGGCATTCCGGATCGCTTTAGCGGCA

GCGGCAGCGGCACCGATTTTACCCTGACCATTAGCCGCCTGGAACCGGAA

GATTTTGCGGTGTATTATTGCCAGCAGCATGATACCAGCCTGACCTTTGG

CGGCGGCACCAAAGTGGAAATTAAATCGTACGTCACCGTCTCTTCACAGG

ATCCCGCCGAGCCCAAATCTCCTGACAAAACTCACACATGCCCACCGTGC

CCAGCACCTGAACTCCTGGGGGGACCGTCAGTCTTCCTCTTCCCCCCAAA

ACCCAAGGACACCCTCATGATCTCCCGGACCCCTGAGGTCACATGCGTGG

TGGTGGACGTGAGCCACGAAGACCCTGAGGTCAAGTTCAACTGGTACGTG

GACGGCGTGGAGGTGCATAATGCCAAGACAAAGCCGCGGGAGGAGCAGTA

CAACAGCACGTACCGTGTGGTCAGCGTCCTCACCGTCCTGCACCAGGACT

GGCTGAATGGCAAGGAGTACAAGTGCAAGGTCTCCAACAAAGCCCTCCCA

GCCCCCATCGAGAAAACCATCTCCAAAGCCAAAGGGCAGCCCCGAGAACC

ACAGGTGTACACCCTGCCCCCATCCCGGGATGAGCTGACCAAGAACCAGG

TCAGCCTGACCTGCCTGGTCAAAGGCTTCTATCCCAGCGACATCGCCGTG

GAGTGGGAGAGCAATGGGCAACCGGAGAACAACTACAAGACCACGCCTCC

CGTGCTGGACTCCGACGGCTCCTTCTTCCTCTACAGCAAGCTCACCGTGG

ACAAGAGCAGGTGGCAGCAGGGGAACGTCTTCTCATGCTCCGTGATGCAT

GAGGCTCTGCACAACCACTACACGCAGAAGAGCCTCTCCCTGTCTCCGGG

TAAAAAGATCCCAAATTTTGGGTGCTGGTGGTGGTTGGTGGAGTCCTGG

CTTGCTATAGCTTGCTAGTAACAGTGGCCTTTATTATTTTTTGGGTGAGG

AGTAAGAGGAGCAGGCTCCTGCACAGTGACTACATGAACATGACTCCCCG

CCGCCCCGGGCCCACCCGCAAGCATTACCAGCCCTATGCCCCACCACGCG

ACTTCGCAGCCTATCGCTCCAAACGGGGCAGAAAGAAACTCCTGTATATA

TTCAAACAACCATTTATGAGACCAGTACAAACTACTCAAGAGGAAGATGG

CTGTAGCTGCCGATTTCCAGAAGAAGAAGAAGGAGGATGTGAACTGAGAG

TGAAGTTCAGCAGGAGCGCAGACGCCCCCGCGTACCAGCAGGGCCAGAAC

CAGCTCTATAACGAGCTCAATCTAGGACGAAGAGAGGAGTACGATGTTTT

GGACAAGAGACGTGGCCGGGACCCTGAGATGGGGGGAAAGCCGAGAAGGA

AGAACCCTCAGGAAGGCCTGTACAATGAACTGCAGAAAGATAAGATGGCG

GAGGCCTACAGTGAGATTGGGATGAAAGGCGAGCGCCGGAGGGGCAAGGG

GCACGATGGCCTTTACCAGGGTCTCAGTACAGCCACCAAGGACACCTACG

ACGCCCTTCACATGCAGGCCCTGCCCCCTCGC

SEQ ID NO: 6 is a nucleic acid encoding an exemplary E2A protein:

CAGTGTACTAATTATGCTCTCTTGAAATTGGCTGGAGATGTTGAGAGCAA

TCCCGGGCCC

SEQ ID NO: 7 is a nucleic acid encoding an exemplary IL-15 protein:

ATGCGGATCAGCAAGCCCCACCTGCGGAGCATCAGCATCCAGTGCTACCT

GTGCCTGCTGCTGAACAGCCACTTCCTGACCGAGGCCGGCATCCACGTGT

TCATCCTGGGCTGCTTCAGCGCCGGACTGCCCAAGACCGAGGCCAACTGG

GTGAACGTGATCAGCGACCTGAAGAAGATCGAGGACCTGATCCAGAGCAT

GCACATCGACGCCACCCTGTACACCGAGAGCGACGTGCACCCCAGCTGCA

AGGTGACCGCCATGAAGTGCTTTCTGCTGGAACTGCAGGTGATCAGCCTG

GAAAGCGGCGACGCCAGCATCCACGACACCGTGGAGAACCTGATCATCCT

GGCCAACAACAGCCTGAGCAGCAACGGCAACGTGACCGAGAGCGGCTGCA

AAGAGTGCGAGGAACTGGAAGAGAAGAACATCAAAGAGTTTCTGCAGAGC

TTCGTGCACATCGTGCAGATGTTCATCAACACCAGCTGA

SEQ ID NO: 8 is a nucleic acid encoding an exemplary S309-CAR-IL-15 protein:

ATGGAGTTTGGGCTGAGCTGGCTTTTTCTTGTGGCTATTTTAAAAGGTGT

CCAGTGCGTCGACCAGGTGCAGCTGGTGCAGAGCGGCGCGGAAGTGAAAA

AACCGGGCGCGAGCGTGAAAGTGAGCTGCAAAGCGAGCGGCTATCCGTTT

ACCAGCTATGGCATTAGCTGGGTGCGCCAGGCGCCGGGCCAGGGCCTGGA

ATGGATGGGCTGGATTAGCACCTATAACGGCAACACCAACTATGCGCAGA

AATTTCAGGGCCGCGTGACCATGACCACCGATACCAGCACCACCACCGGC

TATATGGAACTGCGCCGCCTGCGCAGCGATGATACCGCGGTGTATTATTG

-continued

```
CGCGCGCGATTATACCCGCGGCGCGTGGTTTGGCGAAAGCCTGATTGGCG

GCTTTGATAACTGGGGCCAGGGCACCCTGGTGACCGTGAGCAGCGGTGGT

GGTGGTTCTGGTGGTGGTGGTTCTGGCGGCGGCGGCTCCGGTGGTGGTGG

ATCCGAAATTGTGCTGACCCAGAGCCCGGGCACCCTGAGCCTGAGCCCGG

GCGAACGCGCGACCCTGAGCTGCCGCGCGAGCCAGACCGTGAGCAGCACC

AGCCTGGCGTGGTATCAGCAGAAACCGGGCCAGGCGCCGCGCCTGCTGAT

TTATGGCGCGAGCAGCCGCGCGACCGGCATTCCGGATCGCTTTAGCGGCA

GCGGCAGCGGCACCGATTTTACCCTGACCATTAGCCGCCTGGAACCGGAA

GATTTTGCGGTGTATTATTGCCAGCAGCATGATACCAGCCTGACCTTTGG

CGGCGGCACCAAAGTGGAAATTAAATCGTACGTCACCGTCTCTTCACAGG

ATCCCGCCGAGCCCAAATCTCCTGACAAAACTCACACATGCCCACCGTGC
CCAGCACCTGAACTCCTGGGGGGACCGTCAGTCTTCCTCTTCCCCCCAAA
ACCCAAGGACACCCTCATGATCTCCCGGACCCCTGAGGTCACATGCGTGG

TGGTGGACGTGAGCCACGAAGACCCTGAGGTCAAGTTCAACTGGTACGTG

GACGGCGTGGAGGTGCATAATGCCAAGACAAAGCCGCGGGAGGAGCAGTA

CAACAGCACGTACCGTGTGGTCAGCGTCCTCACCGTCCTGCACCAGGACT

GGCTGAATGGCAAGGAGTACAAGTGCAAGGTCTCCAACAAAGCCCTCCCA

GCCCCCATCGAGAAAACCATCTCCAAAGCCAAAGGGCAGCCCCGAGAACC

ACAGGTGTACACCCTGCCCCCATCCCGGGATGAGCTGACCAAGAACCAGG

TCAGCCTGACCTGCCTGGTCAAAGGCTTCTATCCCAGCGACATCGCCGTG

GAGTGGGAGAGCAATGGGCAACCGGAGAACAACTACAAGACCACGCCTCC

CGTGCTGGACTCCGACGGCTCCTTCTTCCTCTACAGCAAGCTCACCGTGG

ACAAGAGCAGGTGGCAGCAGGGGAACGTCTTCTCATGCTCCGTGATGCAT

GAGGCTCTGCACAACCACTACACGCAGAAGAGCCTCTCCCTGTCTCCGGG

TAAAAAAGATCCCAAATTTTGGGTGCTGGTGGTGGTTGGTGGAGTCCTGG
CTTGCTATAGCTTGCTAGTAACAGTGGCCTTTATTATTTTTTGGGTGAGG
AGTAAGAGGAGCAGGCTCCTGCACAGTGACTACATGAACATGACTCCCCG

CCGCCCCGGGCCCACCCGCAAGCATTACCAGCCCTATGCCCCACCACGCG

ACTTCGCAGCCTATCGCTCCAAACGGGGCAGAAAGAAACTCCTGTATATA

TTCAAACAACCATTTATGAGACCAGTACAAACTACTCAAGAGGAAGATGG

CTGTAGCTGCCGATTTCCAGAAGAAGAAGAAGGAGGATGTGAACTGAGAG
TGAAGTTCAGCAGGAGCGCAGACGCCCCCGCGTACCAGCAGGGCCAGAAC
CAGCTCTATAACGAGCTCAATCTAGGACGAAGAGAGGAGTACGATGTTTT

GGACAAGAGACGTGGCCGGGACCCTGAGATGGGGGGAAAGCCGAGAAGGA

AGAACCCTCAGGAAGGCCTGTACAATGAACTGCAGAAAGATAAGATGGCG

GAGGCCTACAGTGAGATTGGGATGAAAGGCGAGCGCCGGAGGGGCAAGGG

GCACGATGGCCTTTACCAGGGTCTCAGTACAGCCACCAAGGACACCTACG

ACGCCCTTCACATGCAGGCCCTGCCCCCTCGCCAGTGTACTAATTATGCT

CTCTTGAAATTGGCTGGAGATGTTGAGAGCAATCCCGGGCCCATGCGGAT

CAGCAAGCCCCACCTGCGGAGCATCAGCATCCAGTGCTACCTGTGCCTGC

TGCTGAACAGCCACTTCCTGACCGAGGCCGGCATCCACGTGTTCATCCTG
GGCTGCTTCAGCGCCGGACTGCCCAAGACCGAGGCCAACTGGGTGAACGT

GATCAGCGACCTGAAGAAGATCGAGGACCTGATCCAGAGCATGCACATCG

ACGCCACCCTGTACACCGAGAGCGACGTGCACCCCAGCTGCAAGGTGACC

GCCATGAAGTGCTTTCTGCTGGAACTGCAGGTGATCAGCCTGGAAAGCGG

CGACGCCAGCATCCACGACACCGTGGAGAACCTGATCATCCTGGCCAACA

ACAGCCTGAGCAGCAACGGCAACGTGACCGAGAGCGGCTGCAAAGAGTGC

GAGGAACTGGAAGAGAAGAACATCAAAGAGTTTCTGCAGAGCTTCGTGCA

CATCGTGCAGATGTTCATCAACACCAGCTGA
```

SEQ ID NOs: 9 and 10 are SARS-CoV-2 S gene forward and reverse primers, respectively.

SEQ ID NOs: 11-22 are primer sequences for subcloning S protein variants.

DETAILED DESCRIPTION

Recent clinical trials testing cancer immunotherapies have shown promising results for treating infectious diseases. As demonstrated herein, S309-CAR-NK-92MI, a NK-92 cell line capable of producing the IL-2 molecule to sustain its own persistence in vivo, provides a proof-of-concept for using S309-CAR-based cell therapy for treating severe COVID-19 patients. These results were confirmed by using primary NK cells expanded from peripheral blood. The disclosed CARs also demonstrate improved results compared to previous CARs targeting coronavirus spike protein. These experiments provide the basis for additional preclinical studies and a potential clinical application for treating coronavirus infections.

I. Terms

Unless otherwise noted, technical terms are used according to conventional usage. Definitions of common terms in molecular biology may be found in *Lewin's Genes X*, ed. Krebs et al., Jones and Bartlett Publishers, 2009 (ISBN 0763766321); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, Proteomics and Informatics*, 3rd Edition, Springer, 2008 (ISBN: 1402067534), and other similar references.

Unless otherwise explained, all technical and scientific terms used herein have the same meaning as commonly understood by one of ordinary skill in the art to which this disclosure belongs. The singular terms "a," "an," and "the" include plural referents unless the context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description.

Although methods and materials similar or equivalent to those described herein can be used in the practice or testing of the present disclosure, suitable methods and materials are described below. All publications, patent applications, patents, and other references mentioned herein are incorporated by reference in their entirety, as are the GenBank or Protein Databank Accession numbers (as present in the database on Dec. 15, 2020). In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Antibody: A polypeptide ligand comprising at least one variable region that recognizes and binds (such as specifically recognizes and specifically binds) an epitope of an antigen. Mammalian immunoglobulin molecules are composed of a heavy (H) chain and a light (L) chain, each of which has a variable region, termed the variable heavy ($V_H$) region and the variable light ($V_L$) region, respectively. Together, the $V_H$ region and the $V_L$ region are responsible for binding the antigen recognized by the antibody. There are five main heavy chain classes (or isotypes) of mammalian immunoglobulin, which determine the functional activity of an antibody molecule: IgM, IgD, IgG, IgA and IgE.

Antibody variable regions contain "framework" regions and hypervariable regions, known as "complementarity determining regions" or "CDRs." The CDRs are primarily responsible for binding to an epitope of an antigen. The framework regions of an antibody serve to position and align the CDRs in three-dimensional space. The amino acid sequence boundaries of a given CDR can be readily determined using any of a number of well-known numbering schemes, including those described by Kabat et al. (*Sequences of Proteins of Immunological Interest*, U.S. Department of Health and Human Services, 1991; the "Kabat" numbering scheme), Chothia et al. (see Chothia and Lesk, *J Mol Biol* 196:901-917, 1987; Chothia et al., *Nature* 342:877, 1989; and Al-Lazikani et al., (JMB 273,927-948, 1997; the "Chothia" numbering scheme), and the ImMunoGeneTics (IMGT) database (see, Lefranc, *Nucleic Acids Res* 29:207-9, 2001; the "IMGT" numbering scheme). The Kabat and IMGT databases are maintained online.

A single-chain antibody (scFv) is a genetically engineered molecule containing the $V_H$ and $V_L$ domains of one or more antibody(ies) linked by a suitable polypeptide linker as a genetically fused single chain molecule (see, for example, Bird et al., *Science*, 242:423-426, 1988; Huston et al., *Proc. Natl. Acad. Sci.*, 85:5879-5883, 1988; Ahmad et al., *Clin. Dev. Immunol.*, 2012, doi:10.1155/2012/980250; Marbry, *IDrugs*, 13:543-549, 2010). The intramolecular orientation of the $V_H$-domain and the $V_L$-domain in a scFv, is typically not decisive for scFvs. Thus, scFvs with both possible arrangements ($V_H$-domain-linker domain-$V_L$-domain; $V_L$-domain-linker domain-$V_H$-domain) may be used. In a dsFv the $V_H$ and $V_L$ have been mutated to introduce a disulfide bond to stabilize the association of the chains. Diabodies also are included, which are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., *Proc. Natl. Acad. Sci.*, 90:6444-6448, 1993; Poljak et al., *Structure*, 2:1121-1123, 1994).

Antibodies also include genetically engineered forms such as chimeric antibodies (such as humanized murine antibodies) and heteroconjugate antibodies (such as bispecific antibodies). See also, *Pierce Catalog and Handbook*, 1994-1995 (Pierce Chemical Co., Rockford, IL); Kuby, J., *Immunology*, $3^{rd}$ Ed., W.H. Freeman & Co., New York, 1997.

Chimeric antigen receptor (CAR): A chimeric molecule that includes an antigen-binding portion (such as a single domain antibody or scFv) and a signaling domain, such as a signaling domain from a T cell receptor (e.g. CD3ζ). Typically, CARs include an antigen-binding portion, a transmembrane domain, and an intracellular domain. The intracellular domain typically includes a signaling domain having an immunoreceptor tyrosine-based activation motif (ITAM), such as CD3ζ or FcεRIγ. In some instances, the intracellular domain also includes the intracellular portion of at least one additional co-stimulatory domain, such as a co-stimulatory domain from CD28, 4-1BB (CD137), ICOS, OX40 (CD134), CD27, and/or DAP10.

Complementarity determining region (CDR): A region of hypervariable amino acid sequence that defines the binding affinity and specificity of an antibody. The light and heavy chains of a mammalian immunoglobulin each have three CDRs, designated VL-CDR1, VL-CDR2, VL-CDR3 and VH-CDR1, VH-CDR2, VH-CDR3, respectively.

Coronavirus: Coronaviruses are a large family of positive-sense, single-stranded RNA viruses that can infect humans and non-human animals. The viral envelope is composed of a lipid bilayer containing the viral membrane (M), envelope (E) and spike (S) proteins. Most coronaviruses cause mild to moderate upper respiratory tract illness; however, three coronaviruses have emerged that can cause more serious illness and death in humans. These are two severe acute respiratory syndrome coronaviruses (SARS-CoV and SARS-CoV-2) and Middle East respiratory syndrome coronavirus (MERS-CoV). Other coronaviruses that infect humans include human coronavirus HKU1, human coronavirus OC43, human coronavirus 229E, and human coronavirus NL63.

Isolated: An "isolated" biological component, such as a nucleic acid, protein, or organelle, has been substantially separated or purified away from other biological components in the environment (such as a cell) in which the component occurs, e.g., other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids and proteins.

Natural Killer (NK) cells: Cells of the immune system that kill target cells in the absence of a specific antigenic stimulus and without restriction according to MHC class. Target cells can be tumor cells or cells harboring viruses. NK cells are characterized by the presence of CD56 and the absence of CD3 surface markers. NK cells typically comprise approximately 10 to 15% of the mononuclear cell fraction in normal peripheral blood. Historically, NK cells were first identified by their ability to lyse certain tumor cells without prior immunization or activation. NK cells are thought to provide a "back up" protective mechanism against viruses and tumors that might escape the CTL response by down-regulating MHC class I presentation. In addition to being involved in direct cytotoxic killing, NK cells also serve a role in cytokine production, which can be important to control cancer and infection.

In some examples, a "modified NK cell" is a NK cell transduced or transfected with a heterologous nucleic acid (such as one or more of the nucleic acids or vectors disclosed herein) or expressing one or more heterologous proteins (such as one or more CARs disclosed herein). The terms "modified NK cell" and "transduced NK cell" are used interchangeably in some examples herein.

Pharmaceutically acceptable carriers: *Remington: The Science and Practice of Pharmacy*, 22$^{nd}$ ed., London, UK: Pharmaceutical Press (2013), describes compositions and formulations suitable for pharmaceutical delivery of modified immune cells and other compositions disclosed herein. In general, the nature of the carrier will depend on the particular mode of administration being employed. For instance, parenteral formulations usually include pharmaceutically and physiologically acceptable fluids such as water, physiological saline, balanced salt solutions, aqueous dextrose, glycerol, or the like as a vehicle. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Purified: The term purified does not require absolute purity; rather, it is intended as a relative term. Thus, for example, a purified protein, nucleic acid, or cell preparation is one in which the protein, nucleic acid, or cell is more enriched than in its initial environment. In one embodiment, a preparation is purified such that the protein, nucleic acid, or cell represents at least 50% of the total protein, nucleic acid, or cell content of the preparation. Substantial purification denotes purification from other proteins, nucleic acids, or cells. A substantially purified protein, nucleic acid, or cell is at least 60%, 70%, 80%, 90%, 95%, 98%, or 99% pure. Thus, in one specific, non-limiting example, a substantially purified protein, nucleic acid, or cell is 90% free of other components.

Recombinant: A nucleic acid or protein that has a sequence that is not naturally occurring or has a sequence that is made by an artificial combination of two otherwise separated segments of sequence (e.g., a "chimeric" sequence). This artificial combination can be accomplished by chemical synthesis or by the artificial manipulation of isolated segments of nucleic acids, for example, by genetic engineering techniques.

SARS-CoV-2: A virus of the genus betacoronavirus that first emerged in humans in 2019, also referred to as Wuhan coronavirus, 2019-nCoV, or 2019 novel coronavirus. Symptoms of SARS-CoV-2 infection include fever, chills, dry cough, shortness of breath, fatigue, muscle/body aches, headache, new loss of taste or smell, sore throat, nausea or vomiting, and diarrhea. Patients with severe disease can develop pneumonia, multi-organ failure, and death. The SARS-CoV-2 virion includes a viral envelope with large spike glycoproteins. The SARS-CoV-2 genome encodes a canonical set of structural protein genes in the order 5'-spike (S)-envelope (E)-membrane (M)-nucleocapsid (N)-3'.

Spike (S) protein: A class I fusion glycoprotein initially synthesized as a precursor protein of approximately 1256 amino acids for SARS-CoV, and 1273 amino acids for SARS-CoV-2. Individual precursor S polypeptides form a homotrimer and undergo glycosylation and processing to remove the signal peptide, and cleavage by a cellular protease between approximately position 679/680 for SARS-CoV, and 685/686 for SARS-CoV-2, to generate separate S1 and S2 polypeptide chains, which remain associated as S1/S2 protomers within the homotrimer, thereby forming a trimer of heterodimers. The S1 subunit is distal to the virus membrane and contains the receptor-binding domain (RBD) that is believed to mediate virus attachment to its host receptor. The S2 subunit is believed to contain the fusion protein machinery, such as the fusion peptide. S2 also includes two heptad-repeat sequences (HR1 and HR2) and a central helix typical of fusion glycoproteins, a transmembrane domain, and a cytosolic tail domain. An exemplary SARS-CoV-2 spike protein sequence includes GenBank Accession No. QHD43416.1 (the sequence of which is incorporated by reference herein).

Subject: A living multi-cellular vertebrate organism, a category that includes both human and veterinary subjects, including human and non-human mammals.

T cell: A white blood cell (lymphocyte) that is an important mediator of the immune response. T cells include, but are not limited to, CD4$^+$ T cells and CD8$^+$ T cells. A CD4$^+$ T lymphocyte is an immune cell that carries a marker on its surface known as "cluster of differentiation 4" (CD4). These cells, also known as helper T cells, help orchestrate the immune response, including antibody responses as well as killer T cell responses. CD8$^+$ T cells carry the "cluster of differentiation 8" (CD8) marker. In one embodiment, a CD8$^+$ T cell is a cytotoxic T lymphocyte (CTL). In another embodiment, a CD8$^+$ cell is a suppressor T cell.

Activated T cells can be detected by an increase in cell proliferation and/or expression of or secretion of one or more cytokines (such as IL-2, IL-4, IL-6, IFNγ, or TNFα). Activation of CD8$^+$ T cells can also be detected by an increase in cytolytic activity in response to an antigen.

In some examples, a "modified T cell" is a T cell transduced or transfected with a heterologous nucleic acid (such as one or more of the nucleic acids or vectors disclosed herein) or expressing one or more heterologous proteins (such as one or more CARs disclosed herein). The terms "modified T cell" and "transduced T cell" are used interchangeably in some examples herein.

Transduced or Transformed: A transformed cell is a cell into which a nucleic acid molecule has been introduced by molecular biology techniques. As used herein, the terms transduction and transformation encompass all techniques by which a nucleic acid molecule might be introduced into such a cell, including transfection with viral vectors, the use of plasmid vectors, and introduction of DNA by electroporation, lipofection, and particle gun acceleration.

Treating or ameliorating a disease: "Treating" refers to a therapeutic intervention that decreases or inhibits a sign or symptom of a disease or pathological condition after it has begun to develop "Ameliorating" refers to the reduction in the number or severity of signs or symptoms of a disease, such as that caused by SARS coronaviruses.

Vector: A nucleic acid molecule that can be introduced into a host cell (for example, by transfection or transduction), thereby producing a transformed host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant nucleic acid vectors having at least some nucleic acid sequences derived from one or more viruses. A replication deficient viral vector is a vector that requires complementation of one or more regions of the viral genome required for replication due to a deficiency in at least one replication-essential gene function.

II. S309-CAR and S309-CAR Cells

Provided herein are CARs that include a coronavirus spike protein-specific binding portion. In some embodiments, the CAR includes an antigen binding domain including a S309 antibody scFv, a hinge domain, a transmembrane domain, and an intracellular domain. In additional embodiments, the CAR further includes a signal peptide and/or an interleukin-15 domain.

In some embodiments, the antigen binding domain is a coronavirus spike protein-specific scFv from S309 antibody, for example having an amino acid sequence with at least 90% sequence identity (for example, at least 91%, at least 92%, at least 93%, at least 94%, at least 95%, at least 96%, at least 97%, at least 98% at least 99% identity) to amino acids 22-275 of SEQ ID NO: 1 or including or consisting of amino acids 22-275 of SEQ ID NO: 1. In other embodiments, the antigen binding domain includes at least one of the CDR sequences (e.g., at least one of VHCDR1-3 and VLCDR1-3, such as at least 1, 2, 3, 4, 5, or 6 of the CDR sequences) provided in Table 1, and specifically binds to a coronavirus spike protein. In some embodiments, the antigen binding domain includes the variable heavy chain (VH) domain complementarity determining region 1 (CDR1), CDR2 and CDR3 amino acid sequences of amino acid positions 47-54, 72-79, and 118-137 of SEQ ID NO: 1, respectively, and the variable light chain (VL) domain CDR1, CDR2 and CDR3 amino acid sequences of amino acid positions 195-201, 219-221, and 258-265 of SEQ ID NO: 1, respectively.

CD3ζ. In particular examples, the intracellular domain includes domains from CD28, 4-1BB, and CD3ζ. In one non-limiting example, the intracellular domain includes amino acids 550-774 of SEQ ID NO: 1. Other exemplary intracellular regions that can be included are from CD8, CD40, OX-40, ICOS, CD27, DAP10, OX40-L, 4-1BBL, ICOS-L, CD80, CD86, ICAM-1, LFA-1, CD56, CTLA-4, PD-1, TIM-3, NKP30, NKP44, NKP40, NKP46, B7-H3, PD-L1, PD-2, CD70, DAP12, PDK, or FcεRIγ.

In some embodiments, the S309-CAR also includes a signal peptide, which is located N-terminal to the scFv domain. In some examples, the signal sequence is a IgG signal peptide or a GM-CSF signal peptide. In one example, the signal sequence is amino acids 1-19 of SEQ ID NO: 1.

In other embodiments, the S309-CAR further includes a domain that increases survival or persistence of a modified immune cell expressing the CAR. In some examples, the domain is a cytokine, for example, an interleukin (IL), such as IL-15 (e.g., SEQ ID NO: 3) or IL-12. In some examples, the domain is located C-terminal to the CD3ζ domain of the CAR.

In additional embodiments, the CAR further includes an inducible gene that can be used to eliminate CAR expressing cells (e.g., a "suicide" gene). The inducible gene can be activated in the event of off target side effects, such as cytokine release syndrome ("cytokine storm"). In some examples, expression of the suicide gene is inducible by a small molecule, such as tetracycline or doxycycline (a "TET ON" system) or rapamycin. See, e.g., Gargett et al., *Front. Pharmacol.* 5:235, 2014; Stavrou et al., *Mol. Ther.* 6:1266-1276, 2018. In other examples, the suicide gene is inducible by a Fas domain inducible system. In some examples, the inducible suicide domain is located N-terminal or C-terminal to the antigen binding domain of the CAR, while in other examples, the inducible suicide domain is located C-terminal to the CD3ζ domain of the CAR. The inducible suicide domain is separated from the CAR by a self-cleaving peptides (such as a P2A peptide or T2A peptide).

TABLE 1

Location of the CDRs in the S309 scFv sequence (determined using IGMT method)

| CDR | Nucleic Acid Sequence | Amino Acid Sequence |
|---|---|---|
| VH CDR1 | GGCTATCCGTTTACCAGCTATGGC (139-162 of SEQ ID NO: 5) | GYPFTSYG (47-54 of SEQ ID NO: 1) |
| VH CDR2 | ATTAGCACCTATAACGGCAACACC (214-237 of SEQ ID NO: 5) | ISTYNGNT (72-79 of SEQ ID NO: 1) |
| VH CDR3 | GCGCGCGATTATACCCGCGGCGCGTGGT TTGGCGAAAGCCTGATTGGCGGCTTTGA TAAC (352-411 of SEQ ID NO: 5) | ARDYTRGAWFGESLIGG FDN (118-137 of SEQ ID NO: 1) |
| VL CDR1 | CAGACCGTGAGCAGCACCAGC (583-603 of SEQ ID NO: 5) | QTVSSTS (195-201 of SEQ ID NO: 1) |
| VL CDR2 | GGCGCGAGC (655-663 of SEQ ID NO: 5) | GAS (219-221 of SEQ ID NO: 1) |
| VL CDR3 | CAGCAGCATGATACCAGCCTGACC (772-795 of SEQ ID NO: 5) | QQHDTSLT (258-265 OF SEQ ID NO: 1) |

In some embodiments, the hinge domain is an IgG hinge region. In one example, the hinge domain is an IgG1 hinge. Other hinge domains can be used, such as hinge regions from other immunoglobulins (for example, IgG4 or IgD) or a hinge region from CD8, CD28, or CD40. In particular examples, the hinge domain includes amino acids 287-518 of SEQ ID NO: 1.

In additional embodiments, the transmembrane domain is a CD28 transmembrane domain. In one example, the transmembrane domain is from CD28. The transmembrane domain can also be from other proteins, such as CD8, CD4, CD3ζ, CD40, OX40L, 41BBL, ICOS, ICOS-L, CD80, CD86, ICAM-1, LFA-1, ICAM-1, CD56, CTLA-4, PD-1, TIM-3, NKP30, NKP44, NKP40, NKP46, B7-H3, PD-L1, PD-2, and CD70. In some examples, the CD28 transmembrane domain includes amino acids 523-549 of SEQ ID NO: 1.

In further embodiments, the intracellular domain includes one or more intracellular regions from CD28, 4-1BB, and/or In some embodiments, the disclosed CARs further include one or more additional antigen binding domains (for example, the CAR is a bispecific CAR or a tri-specific CAR), which may be N-terminal or C-terminal to the S309 antigen binding domain. In some examples, the CAR includes at least one additional antigen binding domain that specifically binds to a coronavirus spike protein or a variant thereof. In some examples, the additional antigen binding domain is different from the S309 antigen binding domain. In some examples, the additional antigen binding domain specifically binds to a coronavirus spike protein including a D614G amino acid substitution. One of ordinary skill in the art can select D614G antigen binding domains (see, e.g., Cao et al., *bioRxiv*, doi.org/10.1101/2020.09.27.316174, 2020). In other examples, the additional antigen binding domain specifically binds to a coronavirus spike protein from coronavirus lineage B.1.617.2, AY.1, AY.2, or AY.3 (e.g., "delta" variant coronaviruses) or a variant thereof. In other examples, the additional antigen binding domain specifically binds to a coronavirus envelope protein or a variant thereof or a coronavirus membrane protein or a variant thereof. In some embodiments, one or more of the additional antigen binding domains specifically binds to a SARS-CoV-2 protein (such as a spike, envelope, or membrane protein). Any combination of additional antigen binding domains can be included in the CAR, such as one or more antigen binding domains that specifically bind a coronavirus spike protein, one or more antigen binding domains that specifically bind a coronavirus envelope protein, one or more antigen binding domains that specifically bind a coronavirus membrane protein, or any combination thereof. In one example, the CAR includes the S309 antigen binding domain disclosed herein and a second antigen binding domain that specifically binds to a coronavirus spike protein and is different from the S309 antigen binding domain, for example is a CR3022 antigen binding domain (see, e.g., U.S. application Ser. No. 17/399,993, filed Aug. 11, 2021, which is incorporated herein by reference in its entirety).

An exemplary S309-CAR is illustrated in FIG. 1A. In one example, the S309-CAR has an amino acid sequence with at least 90% sequence identity (for example, at least 91%, at least 92%, at least 93%, at least 94%, at least 95%, at least 96%, at least 97%, at least 98% or at least 99% sequence identity) to SEQ ID NO: 1 or SEQ ID NO: 4. In other examples, the S309-CAR includes or consists of the amino acid sequence of SEQ ID NO: 1 or SEQ ID NO: 4.

Also provided are nucleic acids encoding the S309 scFv and S309-CARs disclosed herein. In some examples, the S309 scFV or the antigen binding domain of the CAR is encoded by a nucleic acid including the variable heavy chain (VH) domain complementarity determining region 1 (CDR1), CDR2 and CDR3 nucleic acid sequences of nucleic acid positions 139-162, 514-237, and 352-411 of SEQ ID NO: 5, respectively, and the variable light chain (VL) domain CDR1, CDR2 and CDR3 nucleic acid sequences of nucleic acid positions 583-603, 655-663, and 772-765 of SEQ ID NO: 5, respectively. In particular examples, the S309 scFv encoding sequence is a codon-optimized sequence. In some examples, the S309 scFv is encoded by a nucleic acid sequence with at least 90% sequence identity (for example, at least 91%, at least 92%, at least 93%, at least 94%, at least 95%, at least 96%, at least 97%, at least 98% or at least 99% sequence identity) to nucleotides 58-825 of SEQ ID NO: 5 or includes or consists of nucleotides 58-825 of SEQ ID NO: 5. In other examples, the S309-CAR is encoded by a nucleic acid sequence with at least 90% sequence identity (for example, at least 91%, at least 92%, at least 93%, at least 94%, at least 95%, at least 96%, at least 97%, at least 98% or at least 99% sequence identity) to SEQ ID NO: 5 or SEQ ID NO: 8 or includes or consists of the nucleic acid sequence of SEQ ID NO: 5 or SEQ ID NO: 8.

In some embodiments, a nucleic acid molecule encoding a disclosed CAR is included in an vector (such as a viral vector) for expression in a host cell, such as a NK cell. In some examples, the expression vector includes a promoter operably linked to the nucleic acid molecule encoding the CAR. Additional expression control sequences, such as one or more enhancers, transcription and/or translation terminators, and initiation sequences can also be included in the expression vector. In some embodiments, a nucleic acid encoding a CAR provided herein is included in a viral vector. Examples of suitable virus vectors include retrovirus (e.g., MoMLV or lentivirus), adenovirus, adeno-associated virus, vaccinia virus, and fowlpox vectors. In specific examples, the CAR-encoding nucleic acid is included in a MoMLV vector, such as an SFG retroviral vector, or a pHAGE-CPPT lentiviral vector. In other examples, the vector may be a DNA vector.

In some examples, the vector further includes a nucleic acid sequence encoding at least one additional CAR. In some examples, the additional CAR is specific to a coronavirus antigen, for example, a coronavirus spike protein. In some examples, the one or more additional CARs are included in the vector with a CAR disclosed herein, for example, separated by a self-cleaving peptide, such as a P2A peptide sequence. In one example, the additional CAR is a CR3022-CAR (see, e.g., U.S. application Ser. No. 17/399, 993, filed Aug. 11, 2021, which is incorporated herein by reference in its entirety)

Also provided herein are cells (for example, immune cells) that express the disclosed CARs. In particular embodiments, the cells include NK cells. In one non-limiting embodiment, the cell is an NK-92 cell. NK-92 cells are a NK cell line derived from a patient with non-Hodgkin's lymphoma (e.g., ATCC® CRL-2407™). This cell line has properties of activated NK cells (see, e.g., Gong et al., *Leukemia* 8:652-658, 1994). In another embodiment, the cell is an NK-92MI cell (e.g., ATCC® CRL-2408™). The NK-92MI cell line is an interleukin-2 (IL-2) independent NK cell line, derived from NK-92, which stably expresses human IL-2 (see, e.g., Tam et al., *Hum. Gene Ther.* 10:1359-1373, 1999). NK-92 or NK-92MI cells expressing a CAR (such as a S309-CAR and/or other nucleic acids disclosed herein) can be used herein as an "off the shelf" immunotherapy, since autologous NK cells do not have to be produced for each subject. Other NK cell lines that can be used with the disclosed CARs described herein include NKL, KHYG-1, and YTS cells. In other embodiments, the cells include T cells, NKT cells, or macrophages.

Commonly, NK-92 cells must be irradiated prior to infusion to prevent permanent engraftment. The amount of irradiation required is around 10 Gy. The dose of irradiated NK-92 infusion can be up to $10^{10}$ NK-92 cells/m². Importantly, irradiated NK-92 cells have been shown to be safe for infusion in patients, as demonstrated by several NK-92 clinical trials (NCT00900809, NCT00990717, NCT00995137, and NCT01974479). In some examples, the cells are irradiated following transduction or transfection (e.g., treated with γ-irradiation, such as at a dose of at least 1,000, at least 2,000, at least 3,000, at least 5,000, at least 7,000, at least 8,000, at least 9,000, at least 10,000, at least 11,000, at least 12,000, or at least 15,000 or about 1,000-15,000, 2,000-12,000, 1,000-5,000, 5,000-10,000, or 8,000-12,000, or about 10,000 Rad), for example, prior to administering to a subject.

Figure 4A:
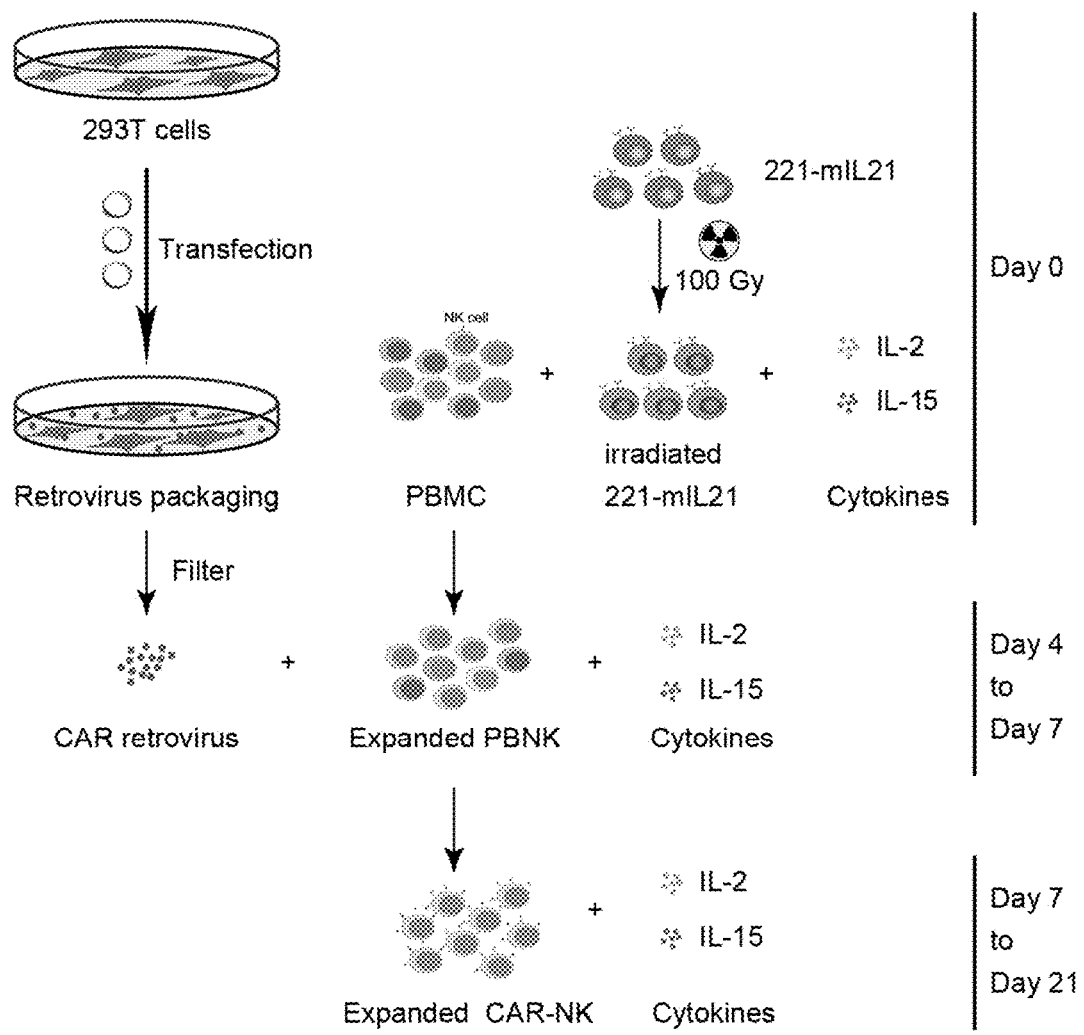
FIGS. 4A-4D illustrate increased killing activity of expanded primary S309-CAR-NK against A549-Spike cell line.

In some non-limiting embodiments, immune cells (such as NK cells or T cells) are transduced with a vector or virus encoding a S309-CAR, including but not limited to SEQ ID NOs: 5 and 8 provided herein. Following transduction, cells expressing the S309-CAR can be detected and/or enriched, for example, by flow cytometry using a labeled antibody that binds to SARS spike protein. In some examples, the transduced cells are expanded, for example, by cell culture for a period of time following transduction. In some examples, some or all of the modified cells are cryopreserved for later use. An exemplary method of producing CAR-NK cells is illustrated in FIG. 4A. However, one of ordinary skill in the art will understand that additional methods of preparing CAR-NK cells can also be successfully utilized. Methods of preparing CAR-T cells are also known.

III. Methods of Treating Coronavirus

Provided herein are methods of treating coronavirus infection (such as SARS-CoV or SARS-CoV2 infection) in a subject using a S309-CAR disclosed herein. In some embodiments, the methods include administering to the subject a composition including a modified cell (such as a modified NK cell) expressing a S309-CAR (for example, transduced with a virus or vector encoding the CAR) and a pharmaceutically acceptable carrier. In other examples, the methods include administering to the subject a pharmaceutical composition including an expression vector encoding a S309-CAR and a pharmaceutically acceptable carrier. In some examples, the subject has been identified as being infected with a coronavirus or is suspected of being infected with a coronavirus. In particular examples, the coronavirus is SARS-CoV-2.

In additional embodiments, the subject may be administered an additional therapeutic agent, for example, modified immune cells expressing a second CAR, which in one non-limiting example is a CAR that specifically binds to D614G mutant coronavirus spike protein. The second CAR may be expressed in the same cells as the S309 CAR disclosed herein, or may be expressed in different cells.

The modified cells or nucleic acids expressing a S309-CAR described herein can be incorporated into pharmaceutical compositions. In some examples, the compositions include a population of cells (such as S309-CAR-NK cells) and a pharmaceutically acceptable carrier. A "pharmaceutically acceptable carrier" includes any and all solvents, dispersion media, coatings, antibacterial and antifungal agents, isotonic and absorption delaying agents, and the like, compatible with pharmaceutical administration (see, e.g., *Remington: The Science and Practice of Pharmacy*, 22$^{nd}$ ed., London, UK: Pharmaceutical Press, 2013). Examples of such carriers or diluents include, but are not limited to, water, saline, Ringer's solutions, dextrose solution, balanced salt solutions, and/or 5% human serum albumin. Liposomes and non-aqueous vehicles such as fixed oils may also be used. Supplementary active compounds can also be incorporated into the compositions. Actual methods for preparing administrable compositions include those provided in *Remington: The Science and Practice of Pharmacy*, 22$^{nd}$ ed., London, UK, Pharmaceutical Press, 2013.

In some examples, the subject being treated is infected with or is suspected to be infected with a coronavirus (such as SARS-CoV or SARS-CoV2). In particular examples, the subject has COVID-19 disease, caused by infection with SARS-CoV2. The population of modified cells (such as S309-CAR-NK cells) is typically administered parenterally, for example intravenously; however, other routes of administration can be utilized. Appropriate routes of administration can be determined based on factors such as the subject, the condition being treated, and other factors.

In some examples, the composition includes about $10^4$ to $10^{12}$ modified immune cells (for example, about $10^4$-$10^8$ cells, about $10^6$-$10^8$ cells, or about $10^6$-$10^{12}$ cells). For example, the composition may be prepared such that about $10^4$ to $10^{10}$ modified cells/kg (such as about $10^4$, $10^5$, $10^6$, $10^7$, or $10^8$ cells/kg) are administered to a subject. In specific examples, the composition includes at least $10^4$, $10^5$, $10^6$, or $10^7$ S309-CAR cells (such as S309-CAR-NK cells). Multiple doses of the population of modified cells can be administered to a subject. For example, S309-CAR cells can be administered daily, every other day, twice per week, weekly, every other week, every three weeks, monthly, or less frequently. A skilled clinician can select an administration schedule based on the subject, the condition being treated, the previous treatment history, and other factors.

In additional examples, the subject is also administered at least one, at least two, at least three, or at least four cytokine(s) (such as IL-2, IL-15, IL-21, and/or IL-12) to support survival and/or growth of the modified immune cells. In specific, non-limiting examples, at least one cytokine includes IL-2 and IL-15. The cytokine(s) are administered before, after, or substantially simultaneously with the modified cells. In specific examples, at least one cytokine (e.g., IL-2) is administered simultaneously with the S309-CAR cells, for example, with S309-CAR-NK cells.

EXAMPLES

The following examples are provided to illustrate certain particular features and/or embodiments. These examples should not be construed to limit the disclosure to the particular features or embodiments described.

Example 1

Materials and Methods

Antibodies and Reagents: PE anti-human CD3 antibody (clone OKT3), FITC and PE/Cy7 anti-human CD56 antibody (clone HCD56, BioLegend), PE anti-human CD69 antibody (clone FN50, BioLegend), PE anti-human CD8a antibody (clone RPA-T8, BioLegend), APC/Fire 750 anti-human CD226 antibody (DNAM-1) (clone 11A8, BioLegend), APC/Fire 750 anti-human KLRG1 (MAFA) antibody (clone SA231A2, BioLegend), BV421 anti-human CD335 (NKp46) antibody (clone 9E2, BioLegend), PE/Cy7 anti-human CD244 (2B4) antibody (clone C1.7, BioLegend), PE anti-human CD152 (CTLA-4) antibody (clone BNI3), APC anti-human CD366 (Tim-3) antibody (clone F38-2E2), PerCP/Cy5.5 anti-human TIGIT (VSTM3) antibody (clone A15153G), FITC anti-human CD223 (LAG-3) antibody (clone 11C3C65, BioLegend), BV510 anti-human CD314 (NKG2D) antibody (clone 1D11), and APC anti-human CD94 (clone DX22, BioLegend) were purchased from BioLegend (San Diego, CA, USA). APC anti-human CD16 antibody (clone 3G8, BD Biosciences), BV711 anti-human CD314 (NKG2D) antibody (clone 1D11, BD Biosciences), and FITC anti-human CD107a antibody (clone H4A3, BD Biosciences) were purchased from BD Biosciences (San Jose, CA, USA). PE anti-human NKG2C/CD159c antibody (clone 134591, R&D Systems) was purchased from R&D Systems. AF647 Goat anti-human IgG(H+L) F(ab')$_2$ fragment antibody was purchased from Jackson ImmunoResearch (West Grove, PA, USA). Anti-SARS-CoV-2 Coronavirus Spike protein (subunit 1) polyclonal antibody was purchased from SinoBiological (Beijing, China). Anti-SARS-CoV-2 Spike RBD rabbit polyclonal antibody was purchased from SinoBiological (Beijing, China). Anti-His mouse monoclonal antibody IgG1 (clone H-3) was purchased from Santa Cruz Biotechnology (Dallas, TX, USA). Alexa Fluor 488 goat anti-rabbit IgG (H+L) and Alexa Fluor 488 goat anti-mouse IgG1 (γ1) were purchased from Fisher Scientific (Waltham, MA).

Cell lines: 293T, A549, HepG2, and NK-92MI cell lines were purchased from the American Type Culture Collection (ATCC). 293T-hACE2 cell line was a gift from Dr. Abraham Pinter (Rutgers-New Jersey Medical School, PHRI). To maintain the stable expression of hACE2, 293T-hACE2 cells were cultured in DMEM (Corning) supplemented with 10% (v/v) fetal bovine serum (FBS), 100 U/mL Penicillin-Streptomycin (Corning), and 1 µg/mL of puromycin at 37° C. under 5% (v/v) $CO_2$.

Generation of transient 293T-hACE2-RBD cell line: To establish the transient 293T-hACE2-RBD cell line, 293T-hACE2 cells were transfected with 0.5 µg of SARS-CoV-2-RBD plasmid (a gift from Dr. Abraham Pinter) in each well in a 24-well plate (Eppendorf) for 48 hours at 37° C. under 5% (v/v) $CO_2$. Transfected cells were harvested after 48 hours and stained with primary anti-RBD (SinoBiological) followed by a goat anti-rabbit fluorophore-conjugated secondary antibody to determine the expression of RBD by flow cytometry.

Generation of stable A549-Spike cell line: pcDNA3.1-SARS-CoV-2 Spike (Addgene plasmid #145302) was used to clone SARS-CoV-2 S gene into the SFG backbone with forward primer TCTAGAGATTACAAGGATGACGAC-GATAAGTAACTCGAGATCGATCCGGAT TAGTCCAAT (SEQ ID NO: 9) and reverse primer GTCGACGCACTGGACACCTTTTAAAATAG (SEQ ID NO:10) using the In-Fusion Cloning kit (Takara Bio). 293T cells were transfected with 3.75 µg SFG-SARS-CoV-2 S, 2.5 µg RDF, and 3.75 µg PegPam3 for 48 hours at 37° C. under 5% (v/v) $CO_2$. The spike retrovirus supernatant was filtered (0.45 µm) and transduced into A549 cells for an additional 48-72 hours at 37° C. under 5% (v/v) $CO_2$. After 2-3 days, transduced cells were changed to fresh DMEM (Corning) supplemented with 10% (v/v) fetal bovine serum (FBS), 100 U/mL Penicillin-Streptomycin (Corning). The spike protein expression was determined by flow cytometry by staining the transduced cells with anti-RBD antibody (SinoBiological) followed by a goat anti-rabbit fluorophore-conjugated secondary antibody. A549-Spike cells were cultured for a few days prior to sorting using anti-RBD. Sorted cells were cultured in DMEM supplemented with 10% (v/v) FBS, and 100 U/mL Penicillin-Streptomycin.

Production of pseudotyped SARS-CoV-2 viral particles: Briefly, 293T cells were transfected using a lentivirus system with a combination of plasmids including p1p1, p1p2, pCMV-luciferase-ecoGFp (a gift from Cornell University), and pcDNA 3.1-SARS-CoV-2 Spike (Addgene plasmid #145032) for 72 hours at 37° C. under 5% (v/v) $CO_2$. The pseudovirus was then filtered (0.45 µm). To confirm the presence of pseudotyped SARS-CoV-2 viral particles, the filtered pseudovirus supernatant was used to transfect 293T-hACE2 for 48 hours at 37° C. under 5% (v/v) $CO_2$. The GFP expression of the transfected 293T-hACE2 cells was observed using an EVOS FL microscope (Life Technologies). The presence of the SARS-CoV-2 pseudovirus was further confirmed by flow cytometry, transfected 293T-hACE2 cells were stained with primary anti-RBD followed by goat anti-rabbit fluorophore-conjugated secondary antibody.

S309-CAR construction and retrovirus production: A codon-optimized DNA fragment was synthesized by GENEWIZ encoding the S309-specific scFv and sub-cloned into the SFG retroviral vector retroviral backbone in-frame with the hinge component of human IgG1, CD28 transmembrane domain, intracellular domain CD28 and 4-1BB, and the ζ chain of the human TCR/CD3 complex. Both the codon-optimized anti-S309 scFv fragment and the SFG vector were digested with restriction endonucleases SalI and BsiWI. SFG-S309 plasmid was transformed into Stbl3 chemically competent cells. Maxiprep was performed to enrich DNA concentration for the transfection step.

To produce S309-CAR retrovirus, 293T cells were transfected with 3.75 µg S309-CAR in SFG backbone, 3.75 µg PegPam3, and 2.5 µg RDF. S309-CAR retrovirus was harvested after 48-72 hours, filtered with a 0.45 µm filter, and transduced to NK-92MI cells in a 24-well plate coated with 0.5 µg/ml of RetroNectin diluted in PBS (Clontech). Two days later, cells were transferred to 75 $cm^2$ flask (Corning) in complete NK-92MI medium (MEM-α with 12.5% (v/v) FBS, 12.5% (v/v) heat inactivated horse serum, 11 µM βME, 2 µM folic acid, and 20 µM inositol. To determine the expression of CAR or to sort S309-CAR-NK-92MI cell line, cells were stained with anti-CD56 and anti-human IgG(H+L) $F(ab')_2$ fragment.

Primary NK cell expansion from peripheral blood: Human blood related work was approved by the Rutgers University Institutional Review Board (IRB). Lymphocyte Separation Medium (Corning) was used to isolate PBMCs from the buffy coats purchased from New York Blood Center. To expand human primary NK cells, $5\times10^6$ cells of isolated PBMCs were cocultured with $10\times10^6$ cells of 100 Gy-irradiated 221-mIL21 cells in 30 mL RPMI 1640 media (Corning) supplemented with 10% (v/v) FBS, 2 mM L-Glutamine (Corning), 100 U/mL Penicillin-Streptomycin, 200 U/mL IL-2 (PeproTech), and 5 ng/mL IL-15 (Peprotech) in a G-REX 6 Multi-well culture plate (Wilson Wolf) at 37° C. under 5% (v/v) $CO_2$. Medium was changed every 3-4 days. An automated cell counter (Nexcelom Bioscience, Lawrence, MA, USA) was used to count the total cell numbers. The NK cell purity was determined by staining cells with anti-CD56 and anti-CD3 followed by flow cytometry analysis.

Transduction of expanded NK cells with S309-CAR: The transduction procedure was previously described, briefly, 293T cells were transfected with a combination of SFG-S309, PegPam3, and RDF. S309-CAR retrovirus was harvested after 48-72 hours, filtered, and transduced to Day 4 of expanded primary NK cells in a 24-well plate coated with 0.5 µg/ml of RetroNectin. Transduced cells were harvested and transferred to a G-Rex well in 30 mL RPMI 1640 media supplemented with 10% (v/v) FBS, 2 mM L-Glutamine, 100 U/mL Penicillin-Streptomycin, 200 U/mL IL-2 (PeproTech), and 5 ng/mL IL-15 (Peprotech). Medium was changed every 3-4 days up to 21 days. Cells were stained for CD56, CD3, and anti-human IgG (H+L) $F(ab')_2$ fragment for the determination of NK cell purity and CAR expression, followed by flow cytometry analysis.

S309-CAR and RBD binding assay: To evaluate the binding activity of CR309-CAR to RBD domain of SARS-CoV-2 S, S309-CAR or NK-92MI ($5\times10^5$) cells were incubated with 5 µg of His-gp70-RBD recombinant protein (a gift from Dr. Abraham Pinter) in DPBS buffer (0.5 mM $MgCl_2$ and 0.9 mM $CaCl_2$ in PBS) in for 30 minutes on ice. Cells were washed twice with PBS, stained with anti-His in FACS buffer (0.2% FBS in PBS) for 30 minutes on ice and then washed twice again with PBS. Cells were then stained with goat anti-mouse (IgG1) secondary antibody in FACS buffer for 30 minutes on ice, washed twice with PBS, and analyzed by Flow Cytometry.

S309-CAR and pseudotyped SARS-CoV-2 S viral particles binding assay: S309-CAR, NK-92MI, and 293T-hACE2 ($5 \times 10^5$) cells were first equilibrated with BM binding media (complete RPMI-1640 containing 0.2% BSA and 10 mM HEPES pH 7.4). Due to the non-specific binding to the S309-CAR of the secondary antibody, cells were first blocked with anti-human IgG(H+L) F(ab')$_2$ fragment for 30 minutes on ice in BM and washed thrice with PBS. Full-length recombinant S protein (Acrobio systems), and S1 subunit recombinant protein (a gift from Dr. Abraham Pinter) were diluted with BM to appropriate concentrations. Filtered pseudotyped SARS-CoV-2 S was used immediately following filtration without further dilution. Pseudotyped SARS-CoV-2 S, or 1 μg of full-length recombinant S protein, or 1 μg of S1 subunit recombinant protein was added to designated wells of a 96-well V bottom plate. The plate was centrifuged at 600×g for 30 minutes at 32° C., and subsequently incubated at 37° C. at 5% $CO_2$ for 1 hour. Cells were washed twice with PBS, stained with anti-S1 (Sino-Biological) in FACS buffer (2% FBS in PBS) for 30 minutes on ice and washed thrice with PBS. Cells were then stained with goat anti-rabbit secondary antibody in FACS buffer for 30 minutes on ice, washed thrice with PBS, and analyzed by Flow Cytometry.

Flow cytometry analysis: Cells were stained and washed as previously described. Cells were analyzed on a FACS LSRII or an LSR Fortessa flow cytometer. PMT voltages were adjusted and compensation values were calculated before data collection. Data were acquired using FACS Diva software and analyzed using FlowJo software.

CD107a degranulation assay: The CD107a degranulation assay was described previously (Song et al., Nat. Commun. 11:3410, 2020). Briefly, NK-92MI or S309-CAR-NK-92MI or CR3022-CAR-NK-92MI cells ($5 \times 10^4$) were cocultured with $1 \times 10^5$ 293T-hACE2, 293T-hACE2-RBD, A549, or A549-Spike cells in the presence of GolgiStop (BD Biosciences) in a V-bottomed 96-well plate in complete RPMI-1640 media at 37° C. under 5% $CO_2$ for 2 hours. The cells were harvested, washed, and stained for CD3, CD56, and CD107a for 30 minutes, and analyzed by flow cytometry.

$Cr^{51}$ release assay: To evaluate the cytotoxic activity of CAR-NK cells, the standard 4-hour $Cr^{51}$ release assay was used. Briefly, target cells were labeled with $Cr^{51}$ at 37° C. for 2 hours and then resuspended at $1 \times 10^5$/mL in NK-92MI culture medium with 10% FBS. Then, $1 \times 10^4$ target cells were incubated with serially diluted CAR-NK or NK-92MI cells at 37° C. under 5% $CO_2$ for 4 hours. After centrifugation, the supernatants were collected and transferred to a 96-well Luma plate and the released $Cr^{51}$ was measured with a gamma counter (Wallac, Turku, Finland). The cytotoxicity (as a percentage) was calculated as follows: [(sample−spontaneous release)/(maximum release−spontaneous release)]×100.

Statistical analysis: Data were represented as means±SEM. The statistical significance was determined using a two-tailed unpaired Student t test, a two-tailed paired Student t test, a two-way ANOVA, where indicated. $p<0.05$ was considered statistically significant.

Example 2

Generation and Characterization of S309-CAR-NK-92MI Cells

Figure 1B:
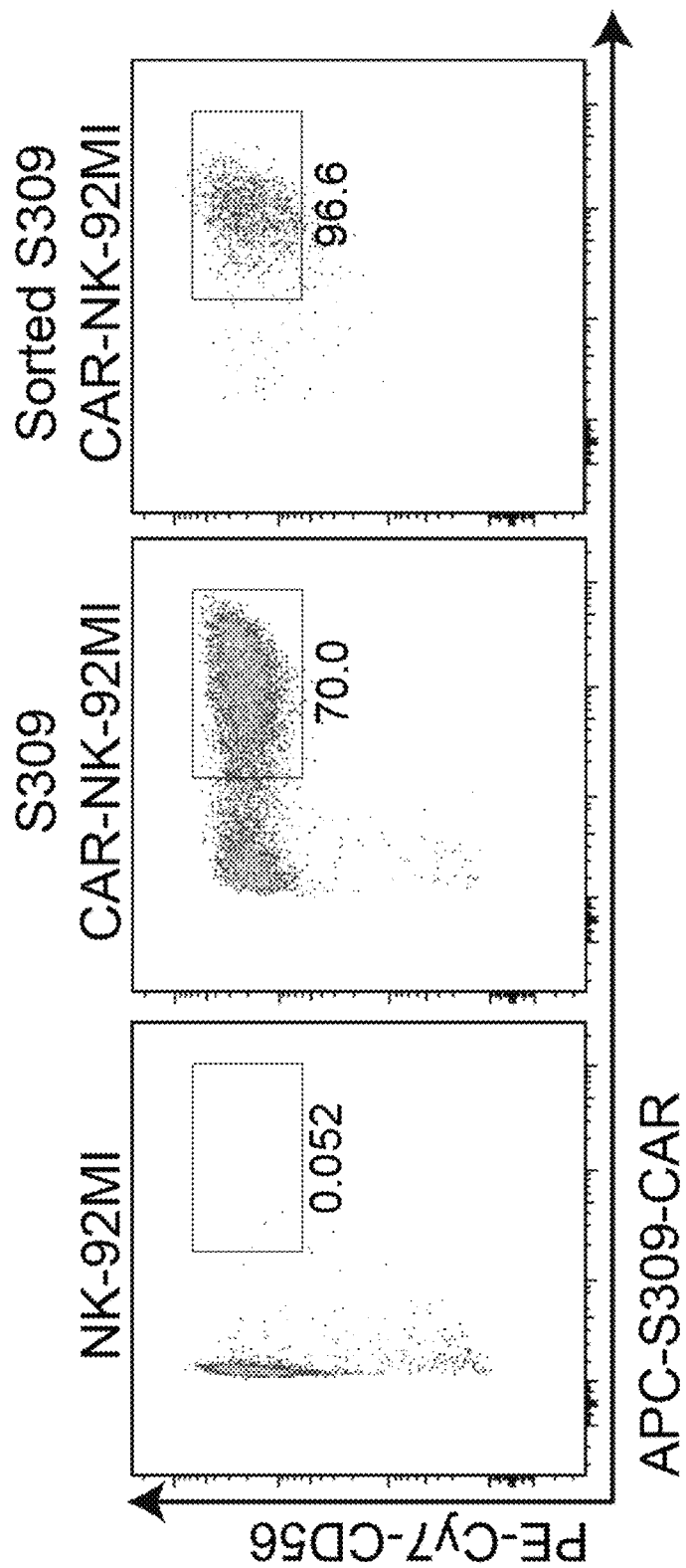

To develop an NK cell-based immunotherapy for a COVID-19 treatment, the scFv domain of S309 was cloned into an SFG retroviral vector that contains a human IgG1 hinge and CH2-CH3 domain, CD28 transmembrane domain and intracellular domain, 4-1BB-Ligand intracellular domain, and CD3ζ intracellular domain (FIG. 1A). S309-CAR-NK cells were generated in the human NK-92MI cell line. 293T cells were transfected with a combination of plasmids containing S309-CAR in the SFG backbone, RDF, and PegPam3, as previously described (Xiong et al., Mol. Ther. 26:963-975, 2018). The SFG retrovirus particles were then used to transduce NK-92MI cells. After 4-5 days, NK-92MI and S309-CAR cells were stained with CD56 and human IgG (H+L) and the CAR expression was analyzed by flow cytometry. Around 70% of $CD56^+$ S309-$CAR^+$ NK-92MI cells were observed (FIG. 1B). Then, the subsequent S309-CAR positive NK-92 cells were sorted by flow cytometry to achieve high CAR expression levels (FIG. 1B).

Figure 1C:
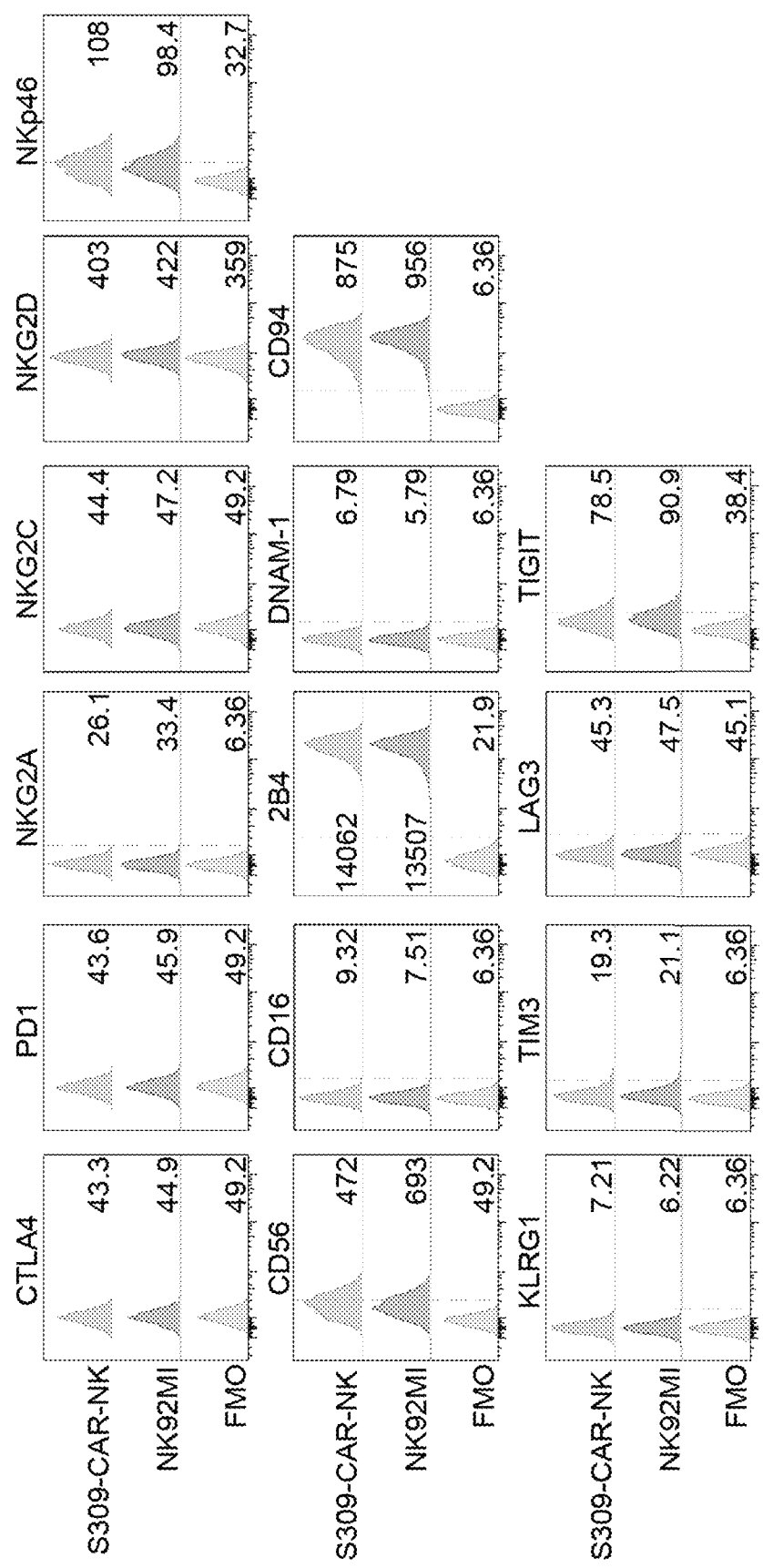

To characterize S309-CAR-NK-92MI cells, the expression of several key immunoreceptors on S309-CAR-NK-92MI cells was examined by flow cytometry. These receptors include TIGIT, LAG-3, TIM-3, KLRG1, CTLA-4, PD-1, CD69, CD8A, NKG2C, CD94, DNAM-1, 2B4, NKG2D, NKp46, and CD16 (FIG. 1C). Overall, the expression of these activating and inhibitory receptors were comparable between parental NK-92MI and S309-CAR-NK-92MI cells, indicating the stable characteristics of NK-92MI at pre- and post-transduction stages.

Figure 2A:
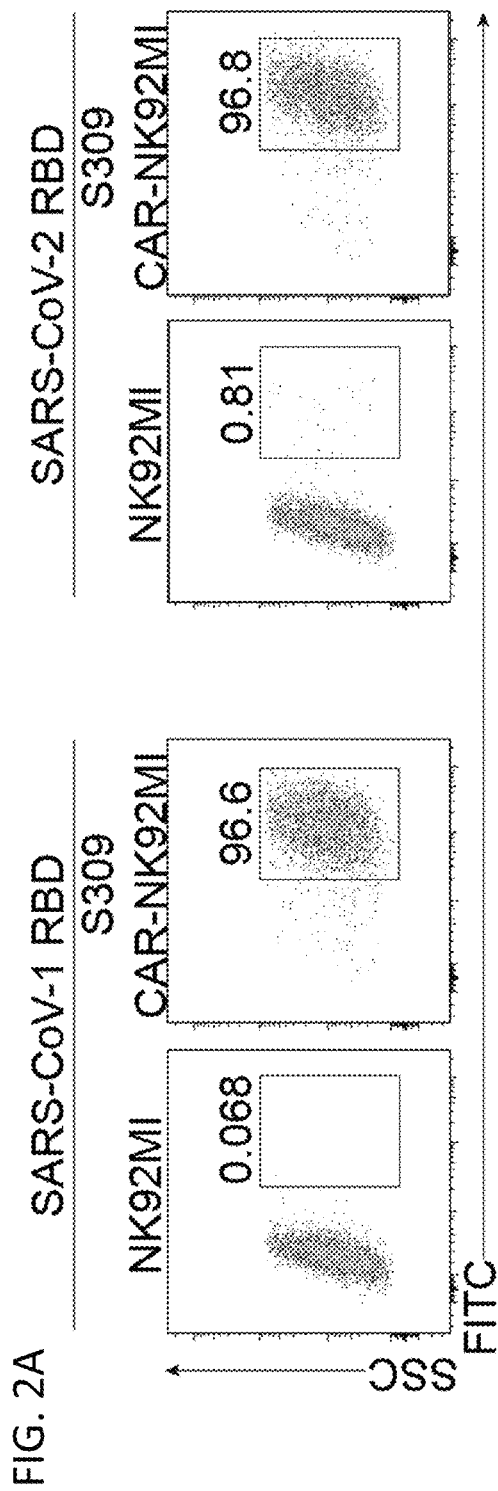

After successful establishment of S309-CAR-NK-92MI cells, the binding ability of S309-CAR-NK cells to the RBD domain of SARS-CoV-2 S protein was assessed. Since S309 neutralizing antibody was isolated from memory B cells of a SARS patient, the recombinant His-RBD protein of SARS-CoV was included as a positive control. S309-CAR-NK-92MI cells and NK-92MI cells were incubated with the His-RBD of SARS-CoV or SARS-CoV-2 and the resulting complex was then recognized by anti-His and its corresponding fluorophore-conjugated-secondary antibody. Flow cytometry was employed to evaluate the binding efficiency of S309-CAR to the RBD of S protein from either SARS-CoV or SARS-CoV-2. S309 recognized and strongly bound to the RBD of both SARS-CoV and SARS-CoV-2 (FIG. 2A).

Figure 2B:
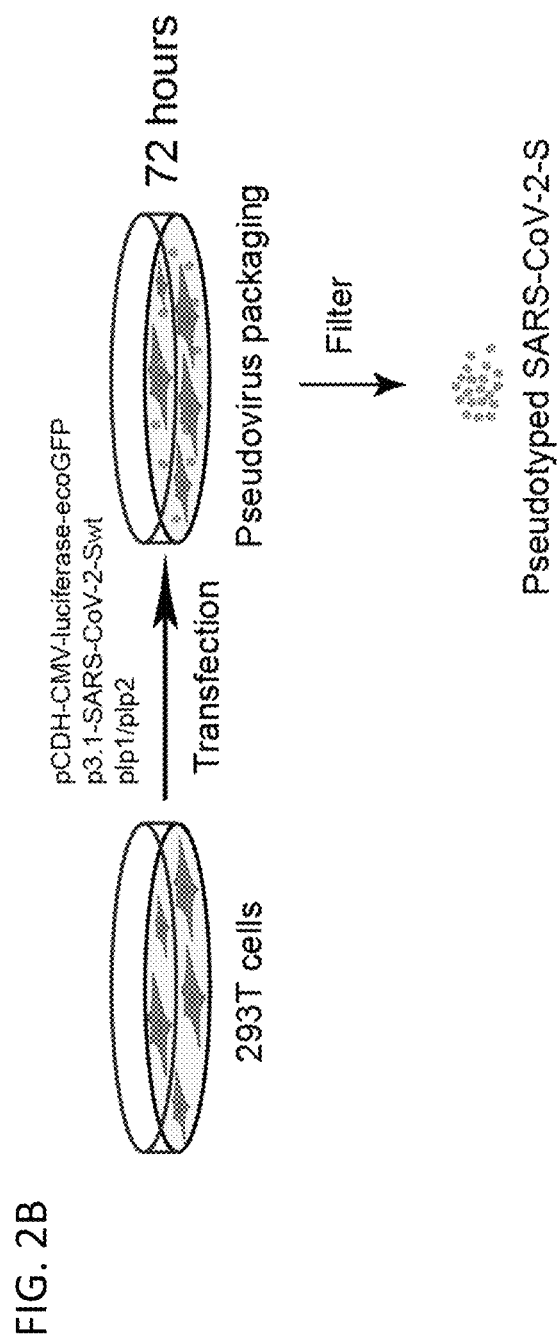

However, the partial RBD domain of SARS-CoV-2 S may not fully reflect the complexity of SARS-CoV-2 viral particles. The binding ability of S309-CAR-NK cells to pseudotyped SARS-CoV-2 S viral particles that we generated in the lab was therefore evaluated. Pseudotyped SARS-CoV-2 viral particles were produced by transfecting 293T cells with a combination of pCMV-luciferase-ecoGFP, pcDNA3.1-SARS-CoV-2 Spike, p1p1, and p1p2 plasmids. The supernatant containing pseudotyped SARS-CoV-2 viral particles were filtered for the pseudovirus binding assay (FIG. 2B). To further confirm the presence of pseudotyped SARS-CoV-2 viral particles, the collected supernatant was used to infect 293T-hACE2 cells. The GFP expression of the infected 293T-hACE2 cells was then observed using EVOS florescence microscope in addition to flow cytometry analysis (data not shown).

Figure 2C:
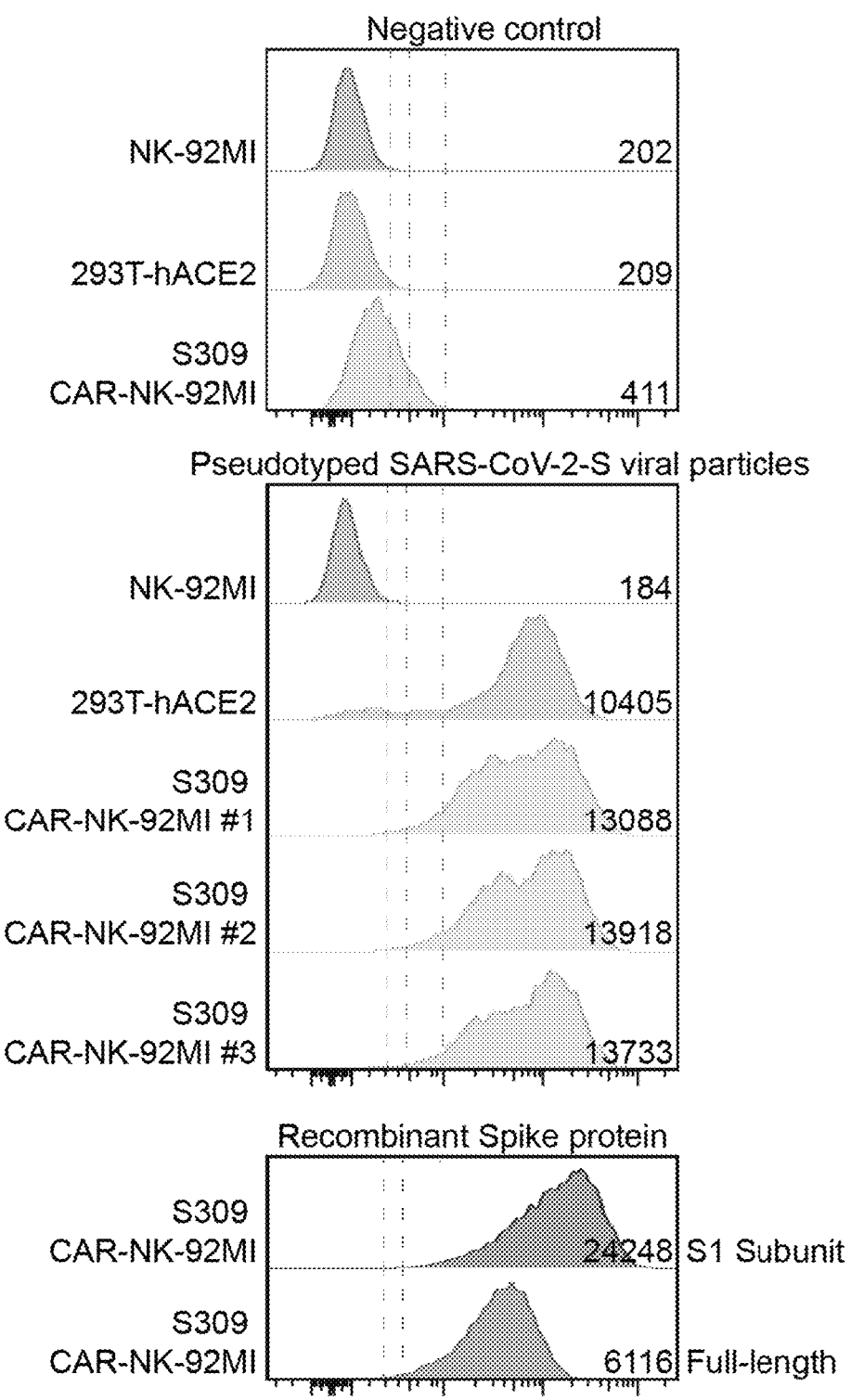

Previous studies showed that the RBD of Spike protein binds to ACE2 and facilitates SARS-CoV-2 entry (Lan et al., Nature 581:215-220, 2020). Thus, 293T-hACE2 was included as a positive control (FIG. 2C). Full-length Spike and RBD-containing S1 subunit recombinant proteins were also included as additional control groups. To evaluate the binding ability of S309-CAR-NK-92MI to the pseudotyped SARS-CoV-2 S virus, S309-CAR-NK-92MI, NK-92MI or 293T-hACE2 were incubated with SARS-CoV-2 S viral particles, S1 subunit, or full-length Spike recombinant protein. The complex can be recognized by anti-S1 subunit antibody and its corresponding fluorophore-conjugated secondary antibody. As expected, S309-CAR-NK-92MI cells were able to bind to the pseudotyped SARS-CoV-2 S viral particles with slightly lower binding efficiency than that of recombinant protein groups (FIG. 2C). Surprisingly, S309-CAR-NK cells showed a stronger binding efficiency to the pseudotyped SARS-CoV-2 viral particles compared to that of 293T-hACE2 cells, suggesting that S309-CAR-NK-92MI may have superior binding capabilities to the SARS-CoV-2 virus compared to the natural receptor, ACE2 (FIG. 2D).

Example 3

Specific Killing of Target Cells by S309-CAR-NK Cells

Figure 3A:
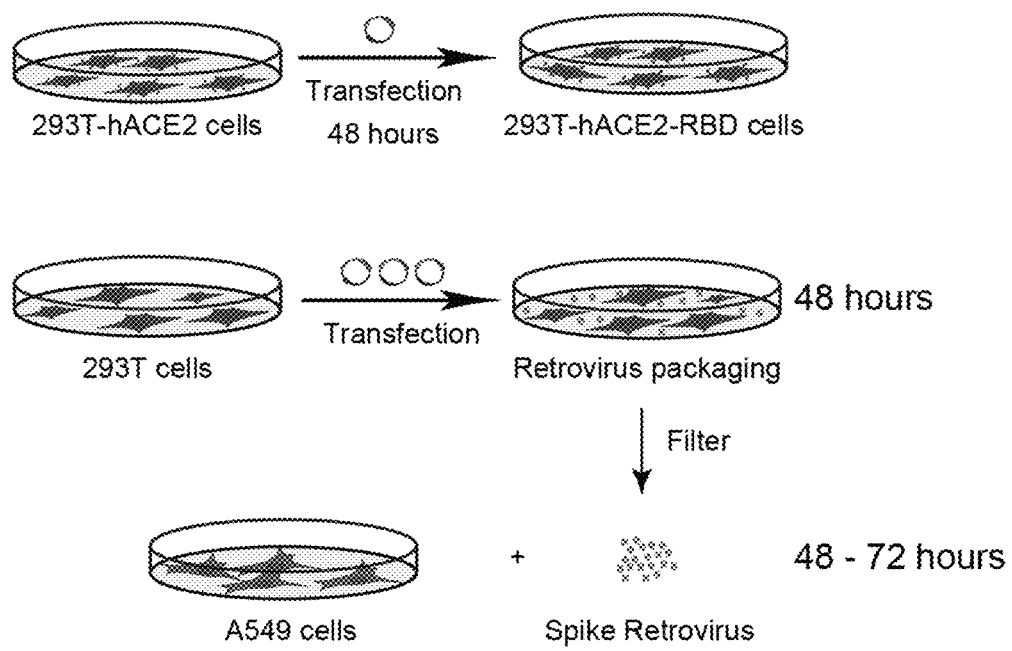
FIGS. 3A-3D demonstrate increased CD107a surface expression and killing activity of S309-CAR-NK-92MI cells against 293T-hACE2-RBD and A549-Spike.
Figure 3B:
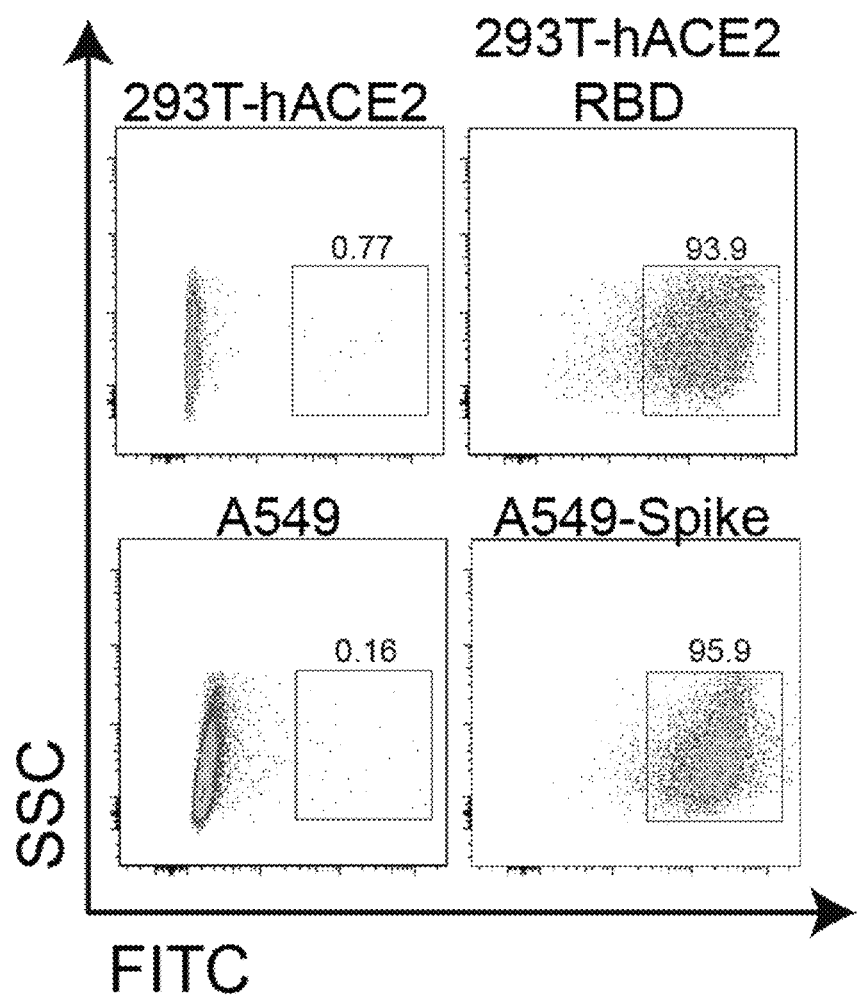

After successful generation of S309-CAR-NK cells and demonstration of recombinant His-RBD protein and pseudotyped SARS-CoV-2 S viral particle binding, S309-CAR-NK cells were evaluated for activation by target cells expressing SARS-CoV-2 Spike protein. To test this, two different cell lines expressing the RBD and spike proteins were generated using 293T-hACE2 and A549 cells, respectively. For the generation of transient 293T-hACE2-RBD cells, an RBD encoding plasmid was transfected into 293T-hACE2 cells (a commonly used cell line for studying the SARS-CoV-2 virus) (FIG. 3A). On average, the transfection efficiencies of RBD proteins on 293T-hACE2 cells were greater than 90% as determined by flow cytometry, immunohistochemistry, and immunocytochemistry confocal microscopy (FIG. 3B). For the generation of the stable A549-Spike cell line, the retrovirus packaging system was used to produce Spike retrovirus that was then transduced into A549 cells (a non-small-cell lung carcinoma cell line) (FIG. 3A). The pre-sorting transduction efficiency was around 70% verified by flow cytometry (data not shown). Transduced A549-Spike cells were subsequently sorted to achieve homogeneously high expression levels of Spike proteins (FIG. 3B).

Figure 3C:
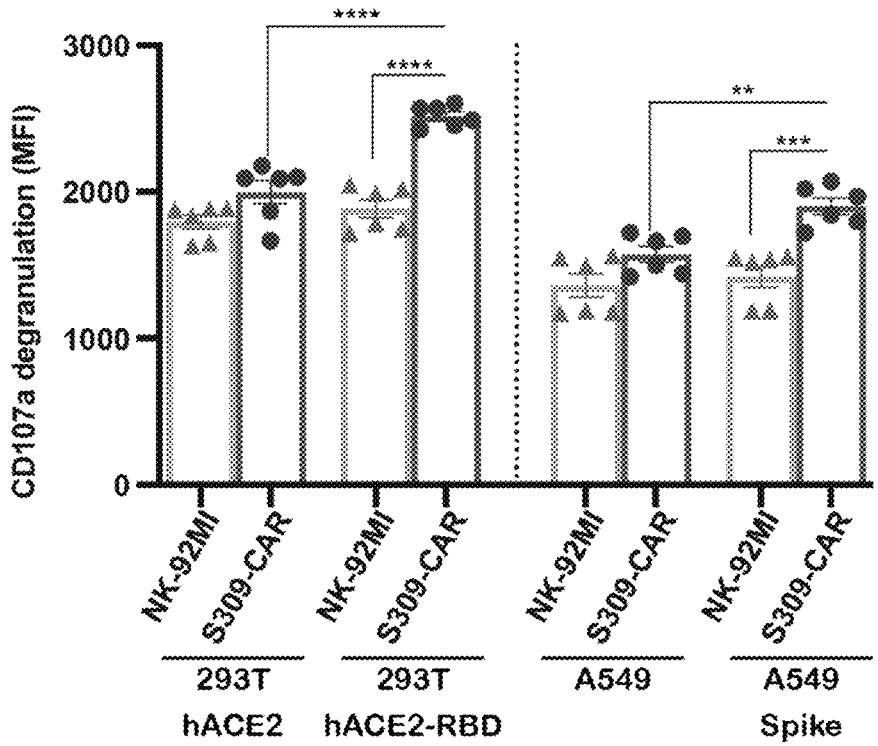
Figure 3C:
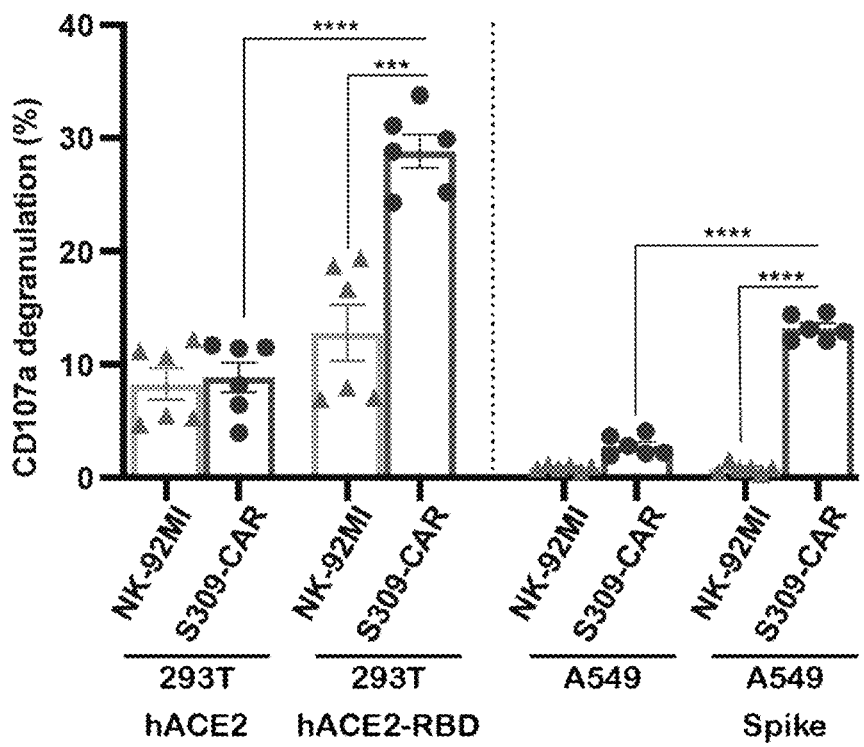

Next, the activation of S309-CAR-NK-92MI cells by 293T-hACE2-RBD or A549-Spike was examined using the CD107a assay. As expected, there was a significant increase in the surface level expression of CD107a molecules on S309-CAR-NK-92MI cells after co-culturing with susceptible 293T-hACE2-RBD or A549-Spike compared to that of wild-type 293T-hACE2 or A549 cells. There was also an increase in total CD107a (percentage and mean fluorescence intensity) on S309-CAR-NK-92MI cells compared to that of NK-92MI cells (FIG. 3C). Interestingly, there was an increased activation level of S309-CAR-NK-92MI cells when cocultured with 293T-hACE2-RBD compared to A549-Spike.

Figure 3D:
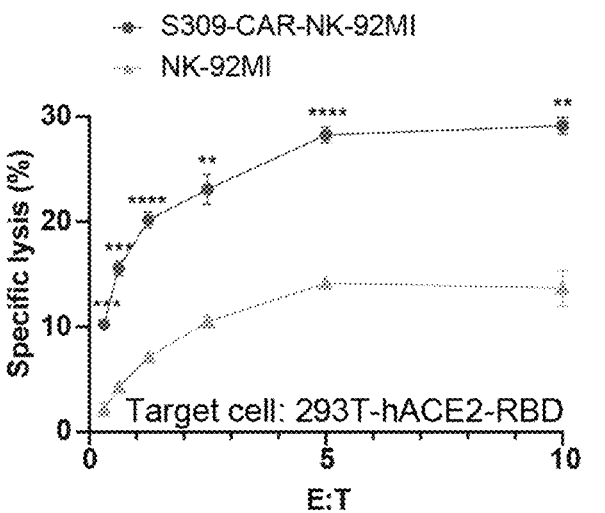
Figure 3D:
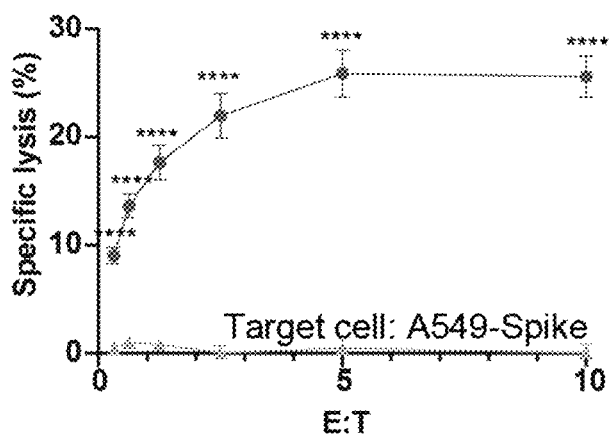
Figure 3D:
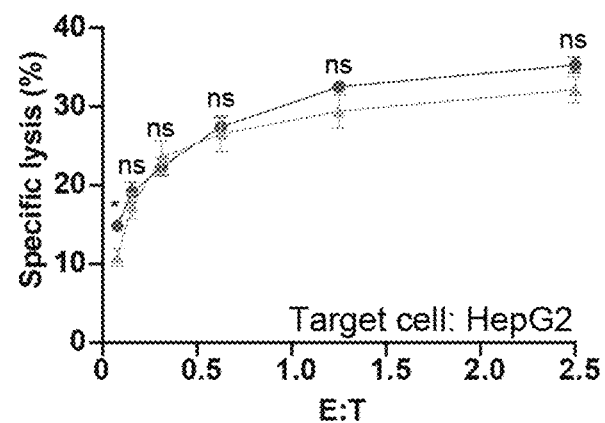

To evaluate the killing activity of S309-CAR-NK-92MI against SARS-CoV-2-protein-expressing target cells, in vitro, the 4-hour Chromium-51 ($Cr^{51}$) release assay (a gold standard assay) was used. The data showed that S309-CAR-NK-92MI cells effectively killed both 293T-hACE2-RBD and A549-Spike cells by in vitro $Cr^{51}$ release assay (FIG. 3D). An irrelevant target cell line, HepG2 (human hepatoma cell line) was used as a negative control, to confirm the specificity of the S309-CAR-NK cells. As expected, no significant difference in the killing activity of S309-CAR-NK-92MI compared to that of wild-type NK-92MI cells (FIG. 3D) was observed.

Figure 4B:
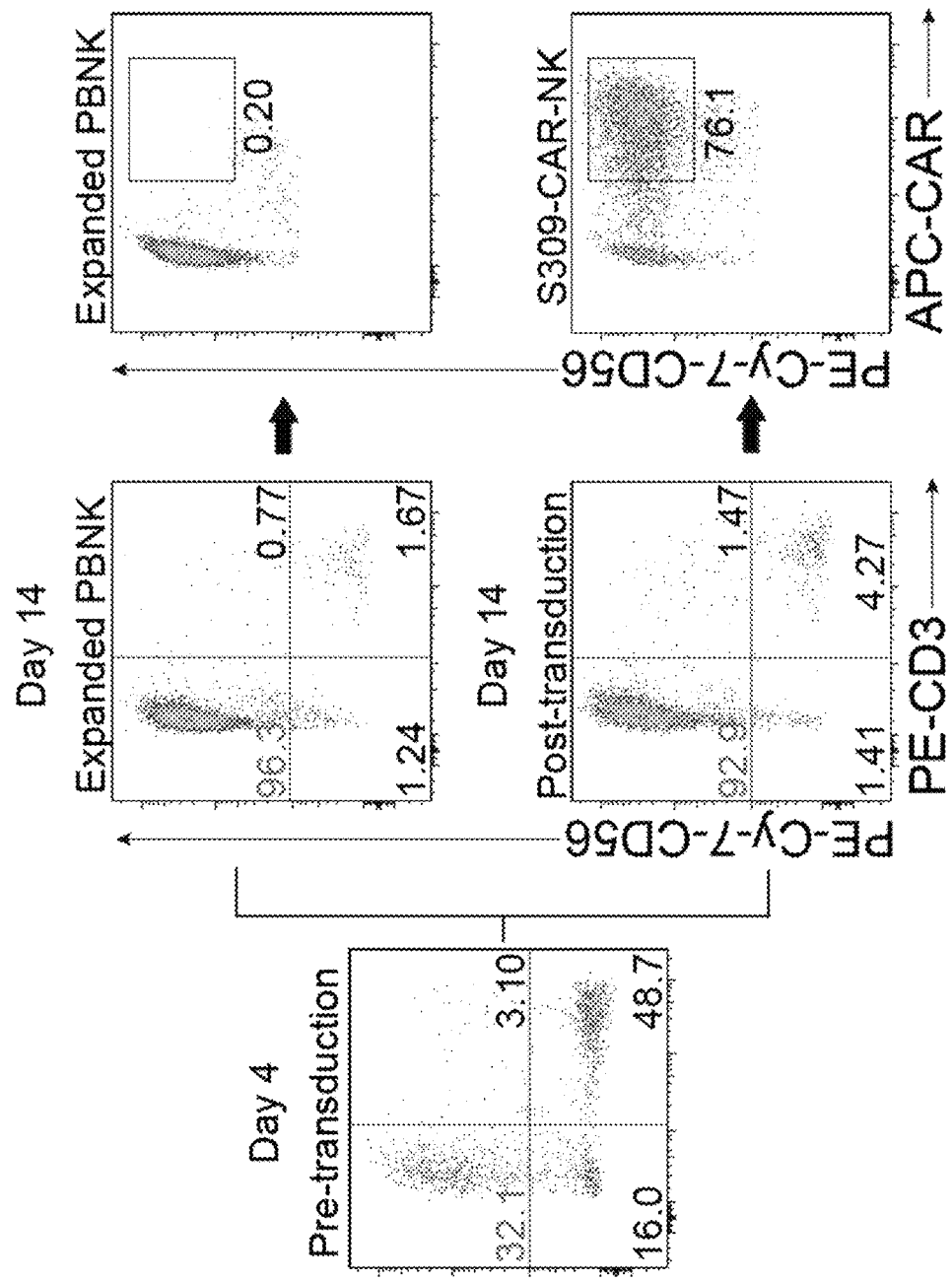

After evaluating the killing function of S309-CAR-NK-92MI cell line, whether the expanded primary S309-CAR-NK cells also have similar killing function against SARS-CoV-2-protein-expressing cells was tested. To expand human primary NK cells from peripheral blood (hereinafter PBNK), peripheral blood mononuclear cells (PBMCs) were isolated from buffy coats from healthy donors and cocultured with 100-Gy irradiated 221-mIL21 feeder cells supplemented with 200 U/mL IL-2 and 5 ng/mL IL-15. In parallel, 293T cells were transfected with a combination of plasmids containing S309-CAR in the SFG backbone, RDF, and PegPam3, as previously described (Xiong et al., *Mol. Ther.* 26:963-975, 2018). The SFG retrovirus particles were used to transduce expanded PBNK cells at Day 4 (FIG. 4A). After 48 hours, primary S309-CAR-NK cells were transferred to a G-Rex plate for continued culturing for 21 days. The NK cell purity and CAR expression were determined using flow cytometry by staining both PBNK and CAR-NK cells with anti-CD56, anti-CD3 and anti-human IgG (H+L). On average, the NK cell purity was around 90% with approximately 80% CAR transduction efficiencies for the S309-CAR-NK (FIG. 4B).

Figure 4C:
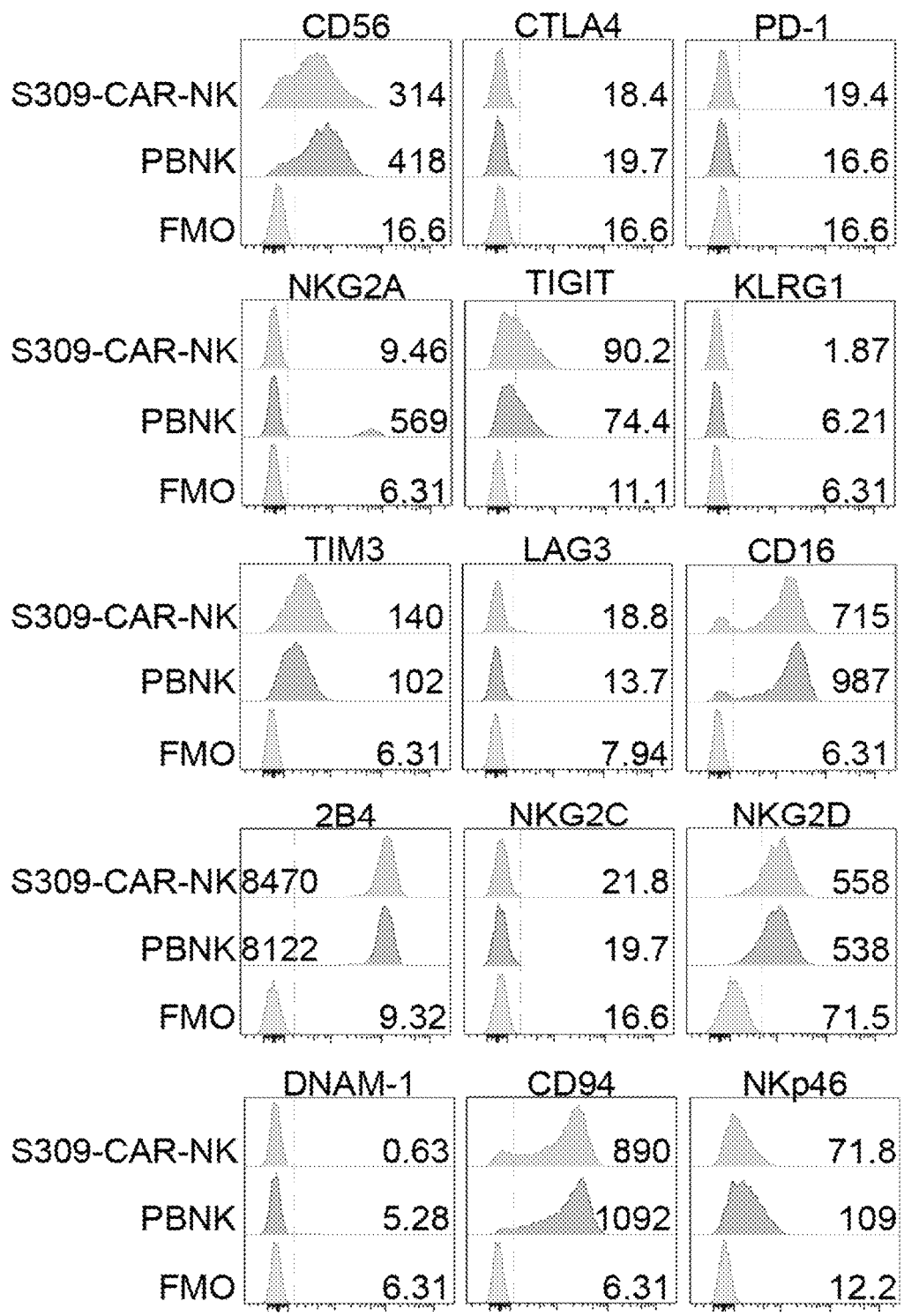

To immunophenotype the expanded primary S309-CAR-NK, both expanded PBNK and S309-CAR-NK were stained cells for various activating and inhibitory receptors, which were determined by flow cytometry. The inhibitory receptors include CTLA4, PD-1, NKG2A, TIGIT, KLRG1, TIM3, and LAG3. The activating receptors include CD16, 2B4, NKG2C NKG2D, DNAM-1, CD94, and NKp46 (FIG. 4C). In general, the expression of these immunomodulatory receptors were comparable between expanded PBNK and S309-CAR-NK cells.

Figure 4D:
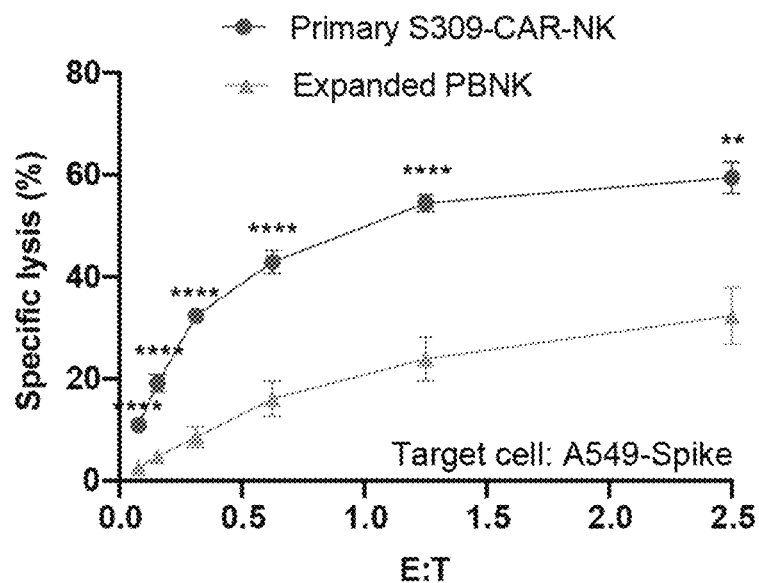

Similar to S309-CAR-NK-92MI, the 4-hour $Cr^{51}$ release assay was used to evaluate the killing function of expanded primary S309-CAR-NK cells. The data showed that S309-CAR-NK cells effectively killed A549-Spike cells compared to expanded PBNK cells (FIG. 4D).

Example 4

Comparison of S309-CAR-NK Cells with Prior CAR-NK Cells

Figure 5A:
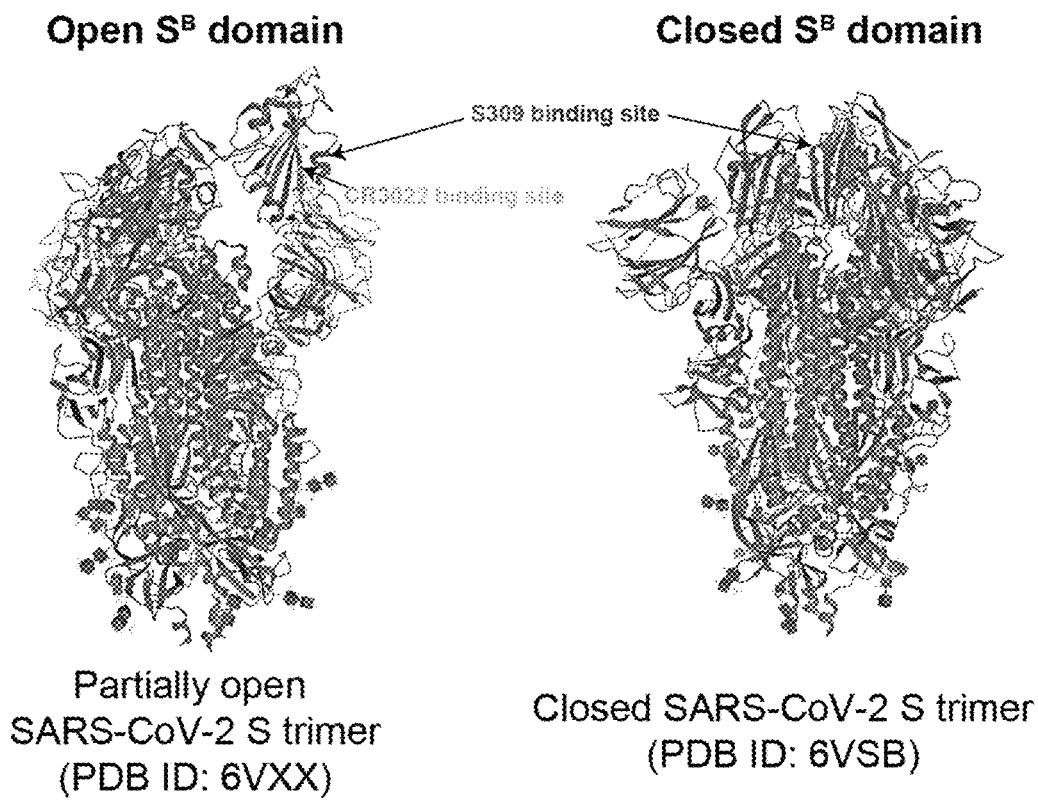
FIGS. 5A-5D show a comparison of S309-CAR-NK cells and CR3022-CAR-NK cells.
Figure 5B:
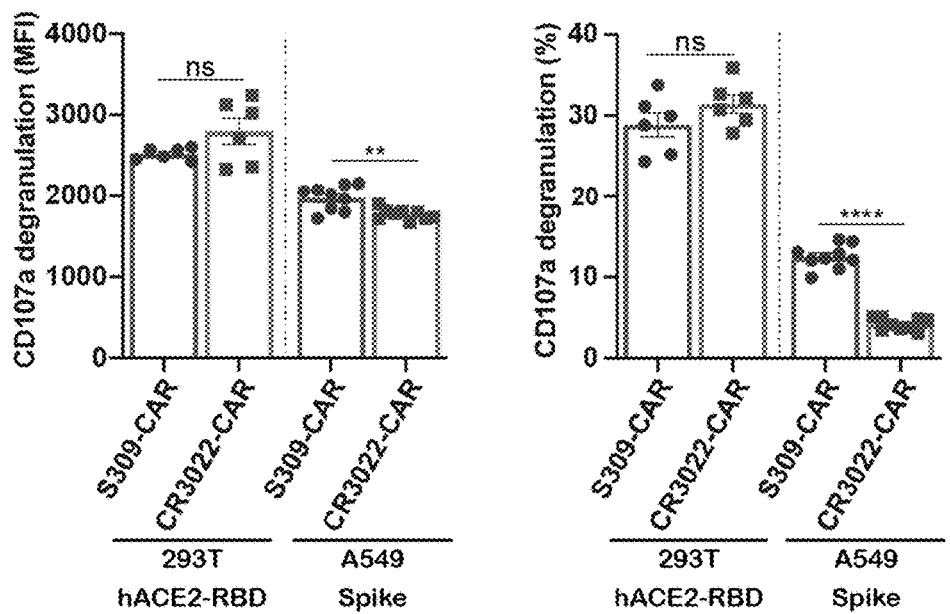

A CR3022-CAR-NK-92MI cell line was previously generated (Ma et al., *bioRxiv*, doi.org/10.1101/2020.08.11.247320, 2020). Previous studies showed that S309 neutralizing antibody recognizes both open and closed conformations of the SARS-CoV-2 S trimer (Pinto et al., *Nature* 583:290-295, 2020); however, CR3022 can only bind to the open state (FIG. 5A). To confirm these findings, the activation levels of S309-CAR-NK-92MI and CR3022-CAR-NK-92MI cells were compared when cocultured with susceptible 293T-hACE2-RBD or A549-Spike target cells. There was not a significant difference in total CD107a, in both percentages and total mean fluorescence intensity (MFI), against the 293T-hACE2-RBD target cell. However, the expression levels of surface CD107a on CR3022-CAR-NK cells were significantly lower when cocultured with A549-Spike compared to that of S309-CAR-NK cells (FIG. 5B). These data suggest that the conformation of the SARS-CoV-2 Spike trimers may play a critical role in CAR recognition and binding ability.

Figure 5C:
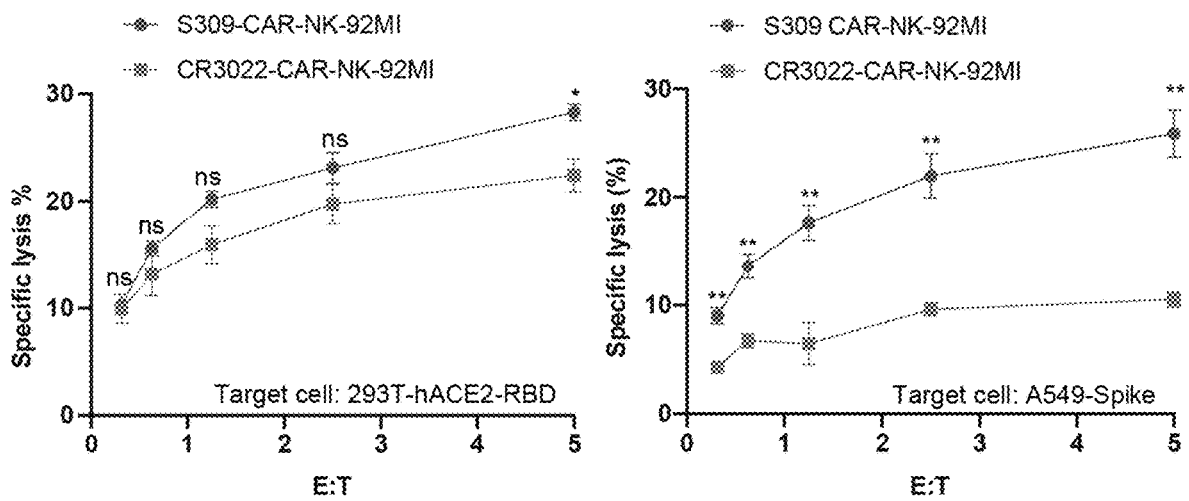
Figure 5D:
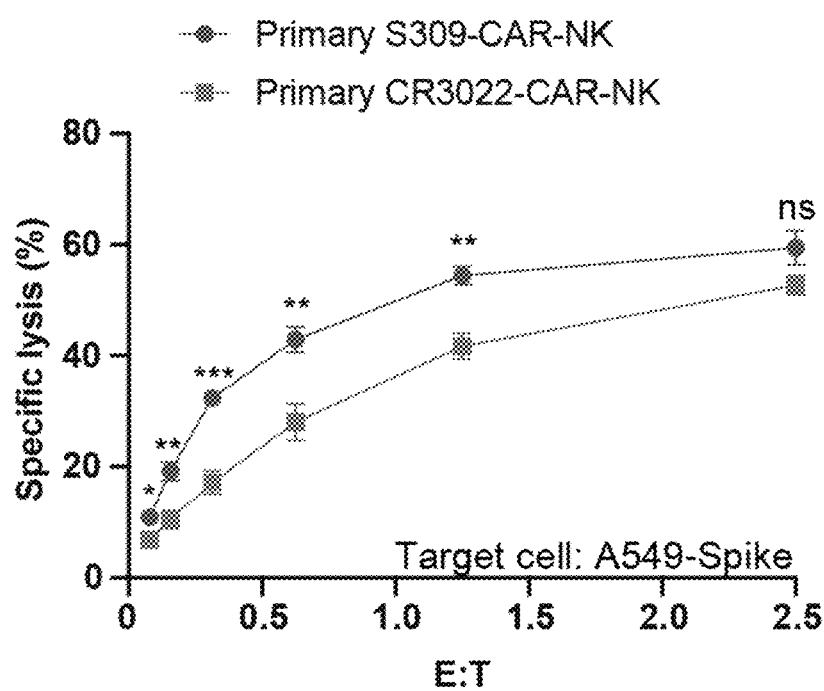

To further evaluate the function of S309-CAR-NK cells, its killing activities were compared to the CR3022-CAR-NK cells. Both 293T-hACE2-RBD and A549-Spike cells were used as susceptible target cells. Consistent with the results in FIG. 5B, a significant decrease in the killing activity of CR3022-CAR-NK cells was observed when A549-Spike cells were the susceptible target cell line in a 4-hour $Cr^{51}$ release assay (FIG. 5C). Considering NK-92MI is a cell line and may not fully reflect the function of primary CAR-NK cells, S309-CAR-NK and CR3022-CAR-NK were also generated from expanded PBNK. Primary S309-CAR-NK cells had better killing activities than primary CR3022-CAR-NK (FIG. 5D).

Example 5

Recognition of SARS-CoV-2 Variants by S309-CAR-NK Cells

Figures 6A, 6B:
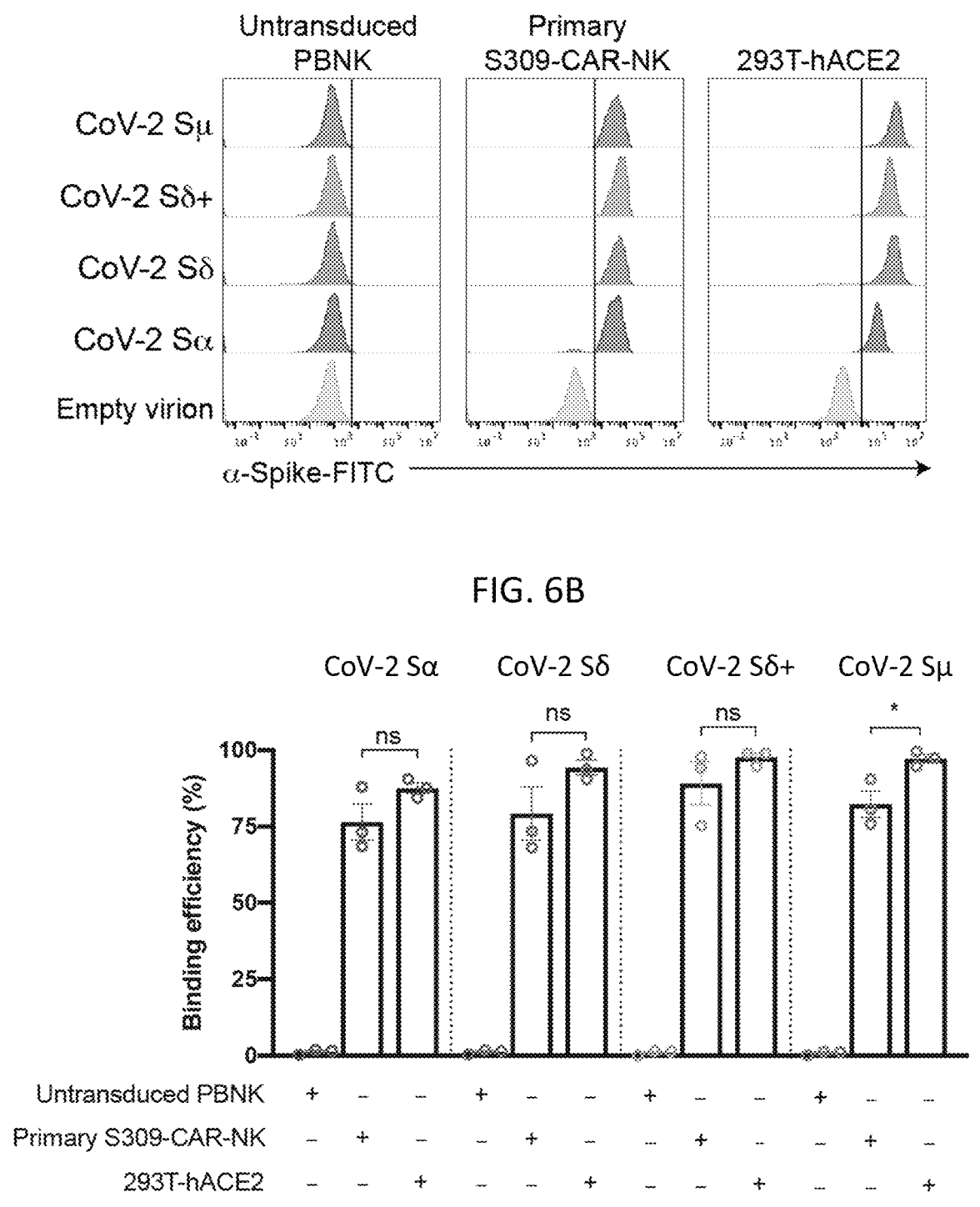

Whether the S309-CAR-NK cells had the ability to recognize different variants of SARS-CoV-2 pseudotyped virus was assessed. Different variants of SARS-CoV-2 pseudovirus bearing mutations were produced by transfecting 293T cells for 72 hours at 37° C. (Table 2). By incubating S309-CAR-NK cells, un-transduced NK cells as negative control, and 293T-hACE2 cells as positive control with different variants of SARS-CoV-2 pseudovirus followed by staining cells with anti-spike and flow cytometry, it was confirmed that S309-CAR-NK cells were effective at binding to the pseudotyped virus of currently existing SARS-CoV-2 variants (FIG. 6A).

TABLE 2

Mutations in the spike protein of different SARS-CoV-2 pseudotyped viruses

| Pseudotyped virus variant | Mutations |
| --- | --- |
| SARS-CoV-2 Sδ | T19R, T95I, G142D, E156G, ΔF157, ΔR158, L452R, T478K, D614G, P681R, D950N |
| SARS-CoV-2 Sδ+ | T19R, T95I, A222V, W258L, K417N, L452R, T478K, E484Q, D614G, P681R, D950N |
| SARS-CoV-2 Sμ | T95I, Y144S, Y145N, R346K, E484K, N501Y, D614G, P681H, D950N |

Figure 7:
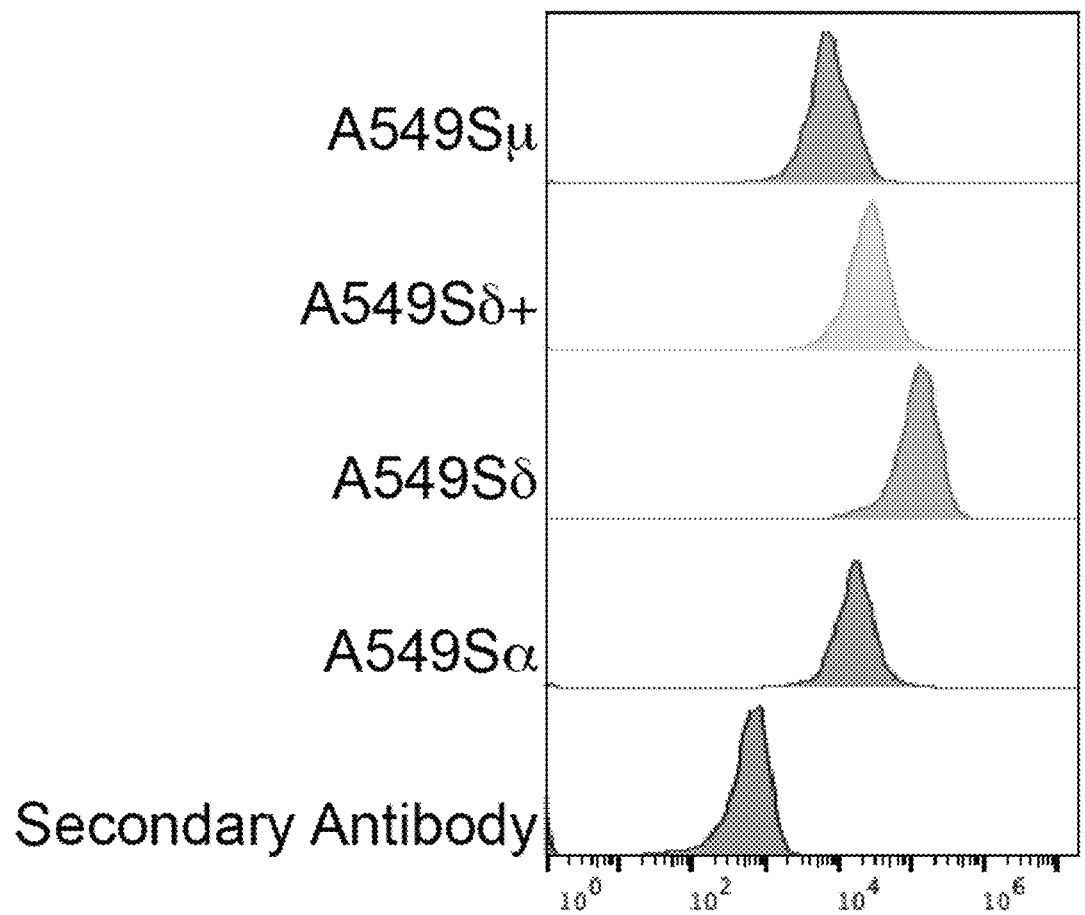
FIG. 7 is a representative histogram of A549 cell lines expressing Sα, Sδ, Sδ+, or Sµ protein pre-sorting. A549 cells were transduced using plasmids containing Sα, Sδ, Sδ+, or Sµ in SFG vector. Transduced cells were harvested, and the expression was confirmed by flow cytometry.

Furthermore, these S309-CAR-NK cells bound to the SARS-CoV-2 pseudotyped virus with similar binding efficiency compared to that of 293T-hACE2, suggesting a role for CAR-NK cells in preventing SARS-CoV-2 from infecting cells expressing ACE2 receptor (FIG. 6B). The plasmids containing Sα, Sδ, Sδ+, or Sμ were subcloned to SFG expression vector to establish A549 cells expressing the aforementioned mutations (Table 3). Briefly, the PCR product of the target insert was fused into the SFG expression vector using In-Fusion. 293T cells were transfected with plasmids containing Sα, Sδ, Sδ+, or Sμ in SFG expression vector for 48 hours at 37° C. Subsequently, the lentivirus supernatant was collected and transduced into parental A549 cell line for an additional 48 hours followed by flow cytometry to confirm the expression of spike protein (FIG. 7). Target cells expressing the mutated spike protein were subsequently sorted for homogenous expression (data not shown).

TABLE 3

Primer sequences for subcloning

| Plasmid/Primer | Sequence (5' - 3') | SEQ ID NO: |
| --- | --- | --- |
| pSFG_SARS-CoV2-Sδ_Forward | TCATGCGGCAGCTGTTGCTCTAGAGATTACAAGGATGACGACGATAAGTAA | 11 |
| pSFG_SARS-CoV2-Sδ_Reverse | CACCAAGAACACAAACATGTCGACGCACTGGACACCTTTTAAAATAGC | 12 |
| pLV_SARS-CoV-2 Sδ_Forward | GGTGTCCAGTGCGTCGACATGTTTGTGTTCTTGGTGTTGCTTCCACTG | 13 |
| pLV_SARS-CoV-2 Sδ_Reverse | ATCCTTGTAATCTCTAGAGCAACAGCTGCCGCATGAGCAG | 14 |
| pSFG SARS-CoV2-Sδ+_Forward | TCCTGCGGCAGCTGCTGCTCTAGAGATTACAAGGATGACGACGATAAGTAA | 15 |
| pSFG_SARS-CoV-2 Sδ+_Reverse | GACCAGGAAGACAAACATGTCGACGCACTGGACACCTTTTAAAATAGC | 16 |
| pCAG_SARS-CoV2-Sδ+_Forward | GGTGTCCAGTGCGTCGACATGTTTGTCTTCCTGGTCCTGCTGC | 17 |
| pCAG_SARS-CoV-2 Sδ+_Reverse | ATCCTTGTAATCTCTAGAGCAGCAGCTGCCGCAGGAGCAG | 18 |
| pSFG_SARS-CoV-2 Sμ_Forward | TCCTGCGGCAGCTGCTGCTCTAGAGATTACAAGGATGACGACGATAAGTAA | 19 |
| pSFG_SARS-CoV-2 Sμ_Reverse | GACCAGGAAGACAAACATGTCGACGCACTGGACACCTTTTAAAATAGC | 20 |
| pCAG_SARS-CoV-2 Sμ_Forward | GGTGTCCAGTGCGTCGACATGTTTGTCTTCCTGGTCCTGCTGC | 21 |
| pCAG_SARS-CoV-2 Sμ_Reverse | ATCCTTGTAATCTCTAGAGCAGCAGCTGCCGCAGGAGCAG | 22 |

The cytotoxicity of S309-CAR-NK cells against the sorted target cell lines can be assessed in vitro using degranulation, chromium release, and lipid bilayer assays. The efficacy of S309-CAR-NK cells in preventing SAR-CoV2 infection and/or prolonging the survival of NSG-hACE2 mice can also be evaluated.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method of treating a subject having or suspected of having a coronavirus infection, comprising administering to the subject an effective amount of a modified immune cell comprising a chimeric antigen receptor comprising at least 93% sequence identity to the amino acid sequence of SEQ ID NO: 1, wherein the chimeric antigen receptor comprises an antigen binding domain comprising the variable heavy chain (VH) domain complementarity determining region 1 (CDR1), CDR2 and CDR3 amino acid sequences of amino acid positions 47-54, 72-79, and 118-137 of SEQ ID NO: 1, respectively, and the variable light chain (VL) domain CDR1, CDR2 and CDR3 amino acid sequences of amino acid positions 195-201, 219-221, and 258-265 of SEQ ID NO: 1, respectively.

2. The method of claim 1, wherein the subject is infected with SARS-COV or SARS-COV-2.

3. A method of treating a subject having or suspected of having a coronavirus infection, comprising administering to the subject an effective amount of a composition comprising: (i) a modified immune cell comprising a chimeric antigen receptor comprising at least 93% sequence identity to the amino acid sequence of SEQ ID NO: 1, wherein the chimeric antigen receptor comprises an antigen binding domain comprising the variable heavy chain (VH) domain complementarity determining region 1 (CDR1), CDR2 and CDR3 amino acid sequences of amino acid positions 47-54, 72-79, and 118-137 of SEQ ID NO: 1, respectively, and the variable light chain (VL) domain CDR1, CDR2 and CDR3 amino acid sequences of amino acid positions 195-201, 219-221, and 258-265 of SEQ ID NO: 1, respectively; and (ii) a pharmaceutically acceptable carrier.

4. The method of claim 1, wherein the antigen binding domain has at least 90% sequence identity to amino acids 22-275 of SEQ ID NO: 1, or comprises or consists of the amino acid sequence of amino acids 22-275 of SEQ ID NO: 1.

5. The method of claim 1, wherein the chimeric antigen receptor comprises the amino acid sequence of SEQ ID NO: 1.

6. The method of claim 1, wherein the chimeric antigen receptor further comprises a signal peptide, an interleukin-15 domain, or both.

7. The method of claim 6, wherein the chimeric antigen receptor has at least 90% sequence identity to the amino acid sequence of SEQ ID NO: 4 .

8. The method of claim 7, wherein the chimeric antigen receptor comprises the amino acid sequence of SEQ ID NO: 4.

9. The method of claim 1, wherein the chimeric antigen receptor consists of the amino acid sequence of SEQ ID NO: 1.

10. The method of claim 3, wherein the antigen binding domain has at least 90% sequence identity to amino acids 22-275 of SEQ ID NO: 1, or comprises or consists of the amino acid sequence of amino acids 22-275 of SEQ ID NO: 1.

11. The method of claim 3, wherein the chimeric antigen receptor comprises the amino acid sequence of SEQ ID NO: 1.

12. The method of claim 3, wherein the chimeric antigen receptor further comprises a signal peptide, an interleukin-15 domain, or both.

13. The method of claim 12, wherein the chimeric antigen receptor has at least 90% sequence identity to the amino acid sequence of SEQ ID NO: 4.

14. The method of claim 13, wherein the chimeric antigen receptor comprises the amino acid sequence of SEQ ID NO: 4.

15. The method of claim 3, wherein the chimeric antigen receptor consists of the amino acid sequence of SEQ ID NO: 1.

16. The method of claim 3, wherein the subject is infected with SARS-COV or SARS-COV-2.

* * * * *

SEQUENCE LISTING

```
<160> NUMBER OF SEQ ID NOS: 22

<210> SEQ ID NO 1
<211> LENGTH: 744
<212> TYPE: PRT
<213> ORGANISM: Artificial Sequence
<220> FEATURE:
<223> OTHER INFORMATION: Exemplary S309-CAR

<400> SEQUENCE: 1

Met Glu Phe Gly Leu Ser Trp Leu Phe Leu Val Ala Ile Leu Lys Gly
1               5                   10                  15

Val Gln Cys Val Asp Gln Val Gln Leu Val Gln Ser Gly Ala Glu Val
            20                  25                  30

Lys Lys Pro Gly Ala Ser Val Lys Val Ser Cys Lys Ala Ser Gly Tyr
        35                  40                  45

Pro Phe Thr Ser Tyr Gly Ile Ser Trp Val Arg Gln Ala Pro Gly Gln
    50                  55                  60

Gly Leu Glu Trp Met Gly Trp Ile Ser Thr Tyr Asn Gly Asn Thr Asn
65                  70                  75                  80

Tyr Ala Gln Lys Phe Gln Gly Arg Val Thr Met Thr Thr Asp Thr Ser
                85                  90                  95

Thr Thr Thr Gly Tyr Met Glu Leu Arg Arg Leu Arg Ser Asp Asp Thr
            100                 105                 110

Ala Val Tyr Tyr Cys Ala Arg Asp Tyr Thr Arg Gly Ala Trp Phe Gly
        115                 120                 125

Glu Ser Leu Ile Gly Gly Phe Asp Asn Trp Gly Gln Gly Thr Leu Val
    130                 135                 140

Thr Val Ser Ser Gly Gly Gly Gly Ser Gly Gly Gly Gly Ser Gly Gly
145                 150                 155                 160

Gly Gly Ser Gly Gly Gly Gly Ser Glu Ile Val Leu Thr Gln Ser Pro
                165                 170                 175

Gly Thr Leu Ser Leu Ser Pro Gly Glu Arg Ala Thr Leu Ser Cys Arg
            180                 185                 190

Ala Ser Gln Thr Val Ser Ser Thr Ser Leu Ala Trp Tyr Gln Gln Lys
        195                 200                 205

Pro Gly Gln Ala Pro Arg Leu Leu Ile Tyr Gly Ala Ser Ser Arg Ala
    210                 215                 220

Thr Gly Ile Pro Asp Arg Phe Ser Gly Ser Gly Ser Gly Thr Asp Phe
225                 230                 235                 240

Thr Leu Thr Ile Ser Arg Leu Glu Pro Glu Asp Phe Ala Val Tyr Tyr
                245                 250                 255

Cys Gln Gln His Asp Thr Ser Leu Thr Phe Gly Gly Gly Thr Lys Val
            260                 265                 270

Glu Ile Lys Ser Tyr Val Thr Val Ser Ser Gln Asp Pro Ala Glu Pro
        275                 280                 285

Lys Ser Pro Asp Lys Thr His Thr Cys Pro Pro Cys Pro Ala Pro Glu
    290                 295                 300
```

```
Leu Leu Gly Gly Pro Ser Val Phe Leu Phe Pro Pro Lys Pro Lys Asp
305                 310                 315                 320

Thr Leu Met Ile Ser Arg Thr Pro Glu Val Thr Cys Val Val Val Asp
                325                 330                 335

Val Ser His Glu Asp Pro Glu Val Lys Phe Asn Trp Tyr Val Asp Gly
            340                 345                 350

Val Glu Val His Asn Ala Lys Thr Lys Pro Arg Glu Glu Gln Tyr Asn
                355                 360                 365

Ser Thr Tyr Arg Val Val Ser Val Leu Thr Val Leu His Gln Asp Trp
370                 375                 380

Leu Asn Gly Lys Glu Tyr Lys Cys Lys Val Ser Asn Lys Ala Leu Pro
385                 390                 395                 400

Ala Pro Ile Glu Lys Thr Ile Ser Lys Ala Lys Gly Gln Pro Arg Glu
                405                 410                 415

Pro Gln Val Tyr Thr Leu Pro Pro Ser Arg Asp Glu Leu Thr Lys Asn
            420                 425                 430

Gln Val Ser Leu Thr Cys Leu Val Lys Gly Phe Tyr Pro Ser Asp Ile
        435                 440                 445

Ala Val Glu Trp Glu Ser Asn Gly Gln Pro Glu Asn Asn Tyr Lys Thr
450                 455                 460

Thr Pro Pro Val Leu Asp Ser Asp Gly Ser Phe Phe Leu Tyr Ser Lys
465                 470                 475                 480

Leu Thr Val Asp Lys Ser Arg Trp Gln Gln Gly Asn Val Phe Ser Cys
                485                 490                 495

Ser Val Met His Glu Ala Leu His Asn His Tyr Thr Gln Lys Ser Leu
            500                 505                 510

Ser Leu Ser Pro Gly Lys Lys Asp Pro Lys Phe Trp Val Leu Val Val
        515                 520                 525

Val Gly Gly Val Leu Ala Cys Tyr Ser Leu Leu Val Thr Val Ala Phe
530                 535                 540

Ile Ile Phe Trp Val Arg Ser Lys Arg Ser Arg Leu Leu His Ser Asp
545                 550                 555                 560

Tyr Met Asn Met Thr Pro Arg Arg Pro Gly Pro Thr Arg Lys His Tyr
                565                 570                 575

Gln Pro Tyr Ala Pro Pro Arg Asp Phe Ala Ala Tyr Arg Ser Lys Arg
            580                 585                 590

Gly Arg Lys Lys Leu Leu Tyr Ile Phe Lys Gln Pro Phe Met Arg Pro
        595                 600                 605

Val Gln Thr Thr Gln Glu Glu Asp Gly Cys Ser Cys Arg Phe Pro Glu
610                 615                 620

Glu Glu Glu Gly Gly Cys Glu Leu Arg Val Lys Phe Ser Arg Ser Ala
625                 630                 635                 640

Asp Ala Pro Ala Tyr Gln Gln Gly Gln Asn Gln Leu Tyr Asn Glu Leu
                645                 650                 655

Asn Leu Gly Arg Arg Glu Glu Tyr Asp Val Leu Asp Lys Arg Arg Gly
            660                 665                 670

Arg Asp Pro Glu Met Gly Gly Lys Pro Arg Arg Lys Asn Pro Gln Glu
        675                 680                 685

Gly Leu Tyr Asn Glu Leu Gln Lys Asp Lys Met Ala Glu Ala Tyr Ser
690                 695                 700

Glu Ile Gly Met Lys Gly Glu Arg Arg Arg Gly Lys Gly His Asp Gly
705                 710                 715                 720
```

```
Leu Tyr Gln Gly Leu Ser Thr Ala Thr Lys Asp Thr Tyr Asp Ala Leu
                725                 730                 735

His Met Gln Ala Leu Pro Pro Arg
            740

<210> SEQ ID NO 2
<211> LENGTH: 20
<212> TYPE: PRT
<213> ORGANISM: Artificial Sequence
<220> FEATURE:
<223> OTHER INFORMATION: E2A protein

<400> SEQUENCE: 2

Gln Cys Thr Asn Tyr Ala Leu Leu Lys Leu Ala Gly Asp Val Glu Ser
1               5                   10                  15

Asn Pro Gly Pro
            20

<210> SEQ ID NO 3
<211> LENGTH: 162
<212> TYPE: PRT
<213> ORGANISM: Homo sapiens

<400> SEQUENCE: 3

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
                20                  25                  30

Val Phe Ile Leu Gly Cys Phe Ser Ala Gly Leu Pro Lys Thr Glu Ala
            35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser

<210> SEQ ID NO 4
<211> LENGTH: 926
<212> TYPE: PRT
<213> ORGANISM: Artificial Sequence
<220> FEATURE:
<223> OTHER INFORMATION: Exemplary S309-CAR-IL-15

<400> SEQUENCE: 4

Met Glu Phe Gly Leu Ser Trp Leu Phe Leu Val Ala Ile Leu Lys Gly
1               5                   10                  15

Val Gln Cys Val Asp Gln Val Gln Leu Val Gln Ser Gly Ala Glu Val
            20                  25                  30

Lys Lys Pro Gly Ala Ser Val Lys Val Ser Cys Lys Ala Ser Gly Tyr
```

```
            35                  40                  45
Pro Phe Thr Ser Tyr Gly Ile Ser Trp Val Arg Gln Ala Pro Gly Gln
 50                  55                  60

Gly Leu Glu Trp Met Gly Trp Ile Ser Thr Tyr Asn Gly Asn Thr Asn
 65                  70                  75                  80

Tyr Ala Gln Lys Phe Gln Gly Arg Val Thr Met Thr Asp Thr Ser
                 85                  90                  95

Thr Thr Thr Gly Tyr Met Glu Leu Arg Arg Leu Arg Ser Asp Asp Thr
                100                 105                 110

Ala Val Tyr Tyr Cys Ala Arg Asp Tyr Thr Arg Gly Ala Trp Phe Gly
                115                 120                 125

Glu Ser Leu Ile Gly Gly Phe Asp Asn Trp Gly Gln Gly Thr Leu Val
                130                 135                 140

Thr Val Ser Ser Gly Gly Gly Gly Ser Gly Gly Gly Ser Gly Gly
145                 150                 155                 160

Gly Gly Ser Gly Gly Gly Ser Glu Ile Val Leu Thr Gln Ser Pro
                165                 170                 175

Gly Thr Leu Ser Leu Ser Pro Gly Glu Arg Ala Thr Leu Ser Cys Arg
                180                 185                 190

Ala Ser Gln Thr Val Ser Ser Thr Ser Leu Ala Trp Tyr Gln Gln Lys
                195                 200                 205

Pro Gly Gln Ala Pro Arg Leu Leu Ile Tyr Gly Ala Ser Ser Arg Ala
210                 215                 220

Thr Gly Ile Pro Asp Arg Phe Ser Gly Ser Gly Ser Gly Thr Asp Phe
225                 230                 235                 240

Thr Leu Thr Ile Ser Arg Leu Glu Pro Glu Asp Phe Ala Val Tyr Tyr
                245                 250                 255

Cys Gln Gln His Asp Thr Ser Leu Thr Phe Gly Gly Gly Thr Lys Val
                260                 265                 270

Glu Ile Lys Ser Tyr Val Thr Val Ser Ser Gln Asp Pro Ala Glu Pro
                275                 280                 285

Lys Ser Pro Asp Lys Thr His Thr Cys Pro Pro Cys Pro Ala Pro Glu
290                 295                 300

Leu Leu Gly Gly Pro Ser Val Phe Leu Phe Pro Pro Lys Pro Lys Asp
305                 310                 315                 320

Thr Leu Met Ile Ser Arg Thr Pro Glu Val Thr Cys Val Val Val Asp
                325                 330                 335

Val Ser His Glu Asp Pro Glu Val Lys Phe Asn Trp Tyr Val Asp Gly
                340                 345                 350

Val Glu Val His Asn Ala Lys Thr Lys Pro Arg Glu Glu Gln Tyr Asn
                355                 360                 365

Ser Thr Tyr Arg Val Val Ser Val Leu Thr Val Leu His Gln Asp Trp
                370                 375                 380

Leu Asn Gly Lys Glu Tyr Lys Cys Lys Val Ser Asn Lys Ala Leu Pro
385                 390                 395                 400

Ala Pro Ile Glu Lys Thr Ile Ser Lys Ala Lys Gly Gln Pro Arg Glu
                405                 410                 415

Pro Gln Val Tyr Thr Leu Pro Pro Ser Arg Asp Glu Leu Thr Lys Asn
                420                 425                 430

Gln Val Ser Leu Thr Cys Leu Val Lys Gly Phe Tyr Pro Ser Asp Ile
                435                 440                 445

Ala Val Glu Trp Glu Ser Asn Gly Gln Pro Glu Asn Asn Tyr Lys Thr
450                 455                 460
```

-continued

```
Thr Pro Pro Val Leu Asp Ser Asp Gly Ser Phe Phe Leu Tyr Ser Lys
465                 470                 475                 480

Leu Thr Val Asp Lys Ser Arg Trp Gln Gln Gly Asn Val Phe Ser Cys
                485                 490                 495

Ser Val Met His Glu Ala Leu His Asn His Tyr Thr Gln Lys Ser Leu
            500                 505                 510

Ser Leu Ser Pro Gly Lys Lys Asp Pro Lys Phe Trp Val Leu Val Val
        515                 520                 525

Val Gly Gly Val Leu Ala Cys Tyr Ser Leu Leu Val Thr Val Ala Phe
530                 535                 540

Ile Ile Phe Trp Val Arg Ser Lys Arg Ser Arg Leu Leu His Ser Asp
545                 550                 555                 560

Tyr Met Asn Met Thr Pro Arg Arg Pro Gly Pro Thr Arg Lys His Tyr
                565                 570                 575

Gln Pro Tyr Ala Pro Pro Arg Asp Phe Ala Ala Tyr Arg Ser Lys Arg
            580                 585                 590

Gly Arg Lys Lys Leu Leu Tyr Ile Phe Lys Gln Pro Phe Met Arg Pro
        595                 600                 605

Val Gln Thr Thr Gln Glu Glu Asp Gly Cys Ser Cys Arg Phe Pro Glu
610                 615                 620

Glu Glu Glu Gly Gly Cys Glu Leu Arg Val Lys Phe Ser Arg Ser Ala
625                 630                 635                 640

Asp Ala Pro Ala Tyr Gln Gln Gly Gln Asn Gln Leu Tyr Asn Glu Leu
                645                 650                 655

Asn Leu Gly Arg Arg Glu Glu Tyr Asp Val Leu Asp Lys Arg Arg Gly
            660                 665                 670

Arg Asp Pro Glu Met Gly Gly Lys Pro Arg Arg Lys Asn Pro Gln Glu
        675                 680                 685

Gly Leu Tyr Asn Glu Leu Gln Lys Asp Lys Met Ala Glu Ala Tyr Ser
690                 695                 700

Glu Ile Gly Met Lys Gly Glu Arg Arg Arg Gly Lys Gly His Asp Gly
705                 710                 715                 720

Leu Tyr Gln Gly Leu Ser Thr Ala Thr Lys Asp Thr Tyr Asp Ala Leu
                725                 730                 735

His Met Gln Ala Leu Pro Pro Arg Gln Cys Thr Asn Tyr Ala Leu Leu
            740                 745                 750

Lys Leu Ala Gly Asp Val Glu Ser Asn Pro Gly Pro Met Arg Ile Ser
        755                 760                 765

Lys Pro His Leu Arg Ser Ile Ser Ile Gln Cys Tyr Leu Cys Leu Leu
        770                 775                 780

Leu Asn Ser His Phe Leu Thr Glu Ala Gly Ile His Val Phe Ile Leu
785                 790                 795                 800

Gly Cys Phe Ser Ala Gly Leu Pro Lys Thr Glu Ala Asn Trp Val Asn
                805                 810                 815

Val Ile Ser Asp Leu Lys Lys Ile Glu Asp Leu Ile Gln Ser Met His
            820                 825                 830

Ile Asp Ala Thr Leu Tyr Thr Glu Ser Asp Val His Pro Ser Cys Lys
        835                 840                 845

Val Thr Ala Met Lys Cys Phe Leu Leu Glu Leu Gln Val Ile Ser Leu
850                 855                 860

Glu Ser Gly Asp Ala Ser Ile His Asp Thr Val Glu Asn Leu Ile Ile
865                 870                 875                 880
```

Leu Ala Asn Asn Ser Leu Ser Ser Asn Gly Asn Val Thr Glu Ser Gly
            885                 890                 895

Cys Lys Glu Cys Glu Glu Leu Glu Glu Lys Asn Ile Lys Glu Phe Leu
        900                 905                 910

Gln Ser Phe Val His Ile Val Gln Met Phe Ile Asn Thr Ser
        915                 920                 925

<210> SEQ ID NO 5
<211> LENGTH: 2232
<212> TYPE: DNA
<213> ORGANISM: Artificial Sequence
<220> FEATURE:
<223> OTHER INFORMATION: Exemplary S309-CAR nucleic acid

<400> SEQUENCE: 5

| | |
|---|---|
| atggagtttg gctgagctg gcttttctt gtggctattt taaaaggtgt ccagtgcgtc | 60 |
| gaccaggtgc agctggtgca gagcggcgcg gaagtgaaaa aaccgggcgc gagcgtgaaa | 120 |
| gtgagctgca aagcgagcgg ctatccgttt accagctatg cattagctg gtgcgccag | 180 |
| gcgccgggcc agggcctgga atggatgggc tggattagca cctataacgg caacaccaac | 240 |
| tatgcgcaga atttcagggg ccgcgtgacc atgaccaccg ataccagcac caccaccggc | 300 |
| tatatggaac tgcgccgcct gcgcagcgat gataccgcgg tgtattattg cgcgcgcgat | 360 |
| tataccgcg gcgcgtggtt tggcgaaagc ctgattggcg gctttgataa ctggggccag | 420 |
| ggcaccctgg tgaccgtgag cagcggtggt ggtggttctg gtggtggtgg ttctggcggc | 480 |
| ggcggctccg gtggtggtgg atccgaaatt gtgctgaccc agagcccggg caccctgagc | 540 |
| ctgagcccgg gcgaacgcgc gaccctgagc tgccgcgcga gccagaccgt gagcagcacc | 600 |
| agcctggcgt ggtatcagca gaaaccgggc caggcgccgc gcctgctgat ttatggcgcg | 660 |
| agcagccgcg cgaccggcat tccggatcgc tttagcggca gcggcagcgg caccgatttt | 720 |
| accctgacca ttagccgcct ggaaccggaa gattttgcgg tgtattattg ccagcagcat | 780 |
| gataccagcc tgacctttgg cggcggcacc aaagtggaaa ttaaatcgta cgtcaccgtc | 840 |
| tcttcacagg atcccgccga gcccaaatct cctgacaaaa ctcacacatg cccaccgtgc | 900 |
| ccagcacctg aactcctggg gggaccgtca gtcttcctct tccccccaaa acccaaggac | 960 |
| accctcatga tctcccggac ccctgaggtc acatgcgtgg tggtggacgt gagccacgaa | 1020 |
| gaccctgagg tcaagttcaa ctggtacgtg gacggcgtgg aggtgcataa tgccaagaca | 1080 |
| aagccgcggg aggagcagta caacagcacg taccgtgtgg tcagcgtcct caccgtcctg | 1140 |
| caccaggact ggctgaatgg caaggagtac aagtgcaagg tctccaacaa agccctccca | 1200 |
| gcccccatcg agaaaaccat ctccaaagcc aaagggcagc cccgagaacc acaggtgtac | 1260 |
| accctgcccc catcccggga tgagctgacc aagaaccagg tcagcctgac ctgcctggtc | 1320 |
| aaaggcttct atcccagcga catcgccgtg gagtgggaga gcaatgggca accggagaac | 1380 |
| aactacaaga ccacgcctcc cgtgctggac tccgacggct ccttcttcct ctacagcaag | 1440 |
| ctcaccgtgg acaagagcag gtggcagcag gggaacgtct tctcatgctc cgtgatgcat | 1500 |
| gaggctctgc acaaccacta cacgcagaag agcctctccc tgtctccggg taaaaaagat | 1560 |
| cccaaatttt gggtgctggt ggtggttggt ggagtcctgg cttgctatag cttgctagta | 1620 |
| acagtggcct ttattatttt tgggtgagg agtaagagga gcaggctcct gcacagtgac | 1680 |
| tacatgaaca tgactccccg ccgccccggg cccacccgca agcattacca gccctatgcc | 1740 |
| ccaccacgcg acttcgcagc ctatcgctcc aaacgggca gaaagaaact cctgtatata | 1800 |

```
ttcaaacaac catttatgag accagtacaa actactcaag aggaagatgg ctgtagctgc    1860
cgatttccag aagaagaaga aggaggatgt gaactgagag tgaagttcag caggagcgca    1920 gacgccccccg cgtaccagca gggccagaac cagctctata acgagctcaa tctaggacga    1980
agagaggagt acgatgtttt ggacaagaga cgtggccggg accctgagat ggggggaaag    2040
ccgagaagga agaaccctca ggaaggcctg tacaatgaac tgcagaaaga taagatggcg    2100
gaggcctaca gtgagattgg gatgaaaggc gagcgccgga ggggcaaggg gcacgatggc    2160
ctttaccagg gtctcagtac agccaccaag gacacctacg acgcccttca catgcaggcc    2220
ctgccccctc gc                                                        2232
```

```
<210> SEQ ID NO 6
<211> LENGTH: 60
<212> TYPE: DNA
<213> ORGANISM: Artificial Sequence
<220> FEATURE:
<223> OTHER INFORMATION: E2A nucleic acid

<400> SEQUENCE: 6
cagtgtacta attatgctct cttgaaattg gctggagatg ttgagagcaa tcccgggccc    60
```

```
<210> SEQ ID NO 7
<211> LENGTH: 489
<212> TYPE: DNA
<213> ORGANISM: Homo sapiens

<400> SEQUENCE: 7
atgcggatca gcaagcccca cctgcggagc atcagcatcc agtgctacct gtgcctgctg    60
ctgaacagcc acttcctgac cgaggccggc atccacgtgt tcatcctggg ctgcttcagc    120
gccggactgc ccaagaccga ggccaactgg gtgaacgtga tcagcgacct gaagaagatc    180
gaggacctga tccagagcat gcacatcgac gccaccctgt acaccgagag cgacgtgcac    240
cccagctgca aggtgaccgc catgaagtgc tttctgctgg aactgcaggt gatcagcctg    300
gaaagcggcg acgccagcat ccacgacacc gtggagaacc tgatcatcct ggccaacaac    360
agcctgagca gcaacggcaa cgtgaccgag agcggctgca aagagtgcga ggaactggaa    420
gagaagaaca tcaaagagtt tctgcagagc ttcgtgcaca tcgtgcagat gttcatcaac    480
accagctga                                                            489
```

```
<210> SEQ ID NO 8
<211> LENGTH: 2781
<212> TYPE: DNA
<213> ORGANISM: Artificial Sequence
<220> FEATURE:
<223> OTHER INFORMATION: Exemplary S309-CAR-IL-15 nucleic acid

<400> SEQUENCE: 8
atggagtttg gctgagctg cttttttctt gtggctattt taaaaggtgt ccagtgcgtc     60
gaccaggtgc agctggtgca gagcggcgcg gaagtgaaaa aaccgggcgc gagcgtgaaa    120
gtgagctgca aagcgagcgg ctatccgttt accagctatg cattagctg gtgcgccag     180 gcgccgggcc agggcctgga atggatggc tggattagca cctataacgg caacaccaac    240
tatgcgcaga atttcagggg ccgcgtgacc atgaccaccg ataccagcac caccaccggc    300
tatatggaac tgcgccgcct gcgcagcgat gataccgcgg tgtattattg cgcgcgcgat    360 tatcccgcg gcgcgtggtt tggcgaaagc ctgattggcg gctttgataa ctggggccag    420
ggcacccctg tgaccgtgag cagcggtggt ggtggttctg gtggtggtgg ttctggcggc    480
```

| | |
|---|---|
| ggcggctccg gtggtggtgg atccgaaatt gtgctgaccc agagcccggg caccctgagc | 540 |
| ctgagcccgg gcgaacgcgc gaccctgagc tgccgcgcga gccagaccgt gagcagcacc | 600 |
| agcctggcgt ggtatcagca gaaaccgggc caggcgccgc gcctgctgat ttatggcgcg | 660 |
| agcagccgcg cgaccggcat tccggatcgc tttagcggca gcggcagcgg caccgatttt | 720 |
| accctgacca ttagccgcct ggaaccggaa gattttgcgg tgtattattg ccagcagcat | 780 |
| gataccagcc tgacctttgg cggcggcacc aaagtggaaa ttaaatcgta cgtcaccgtc | 840 |
| tcttcacagg atcccgccga gcccaaatct cctgacaaaa ctcacacatg cccaccgtgc | 900 |
| ccagcacctg aactcctggg gggaccgtca gtcttcctct tccccccaaa acccaaggac | 960 |
| accctcatga tctcccggac ccctgaggtc acatgcgtgg tggtggacgt gagccacgaa | 1020 |
| gaccctgagg tcaagttcaa ctggtacgtg gacggcgtgg aggtgcataa tgccaagaca | 1080 |
| aagccgcggg aggagcagta caacagcacg taccgtgtgg tcagcgtcct caccgtcctg | 1140 |
| caccaggact ggctgaatgg caaggagtac aagtgcaagg tctccaacaa agccctccca | 1200 |
| gcccccatcg agaaaaccat ctccaaagcc aaagggcagc ccgagaacc acaggtgtac | 1260 |
| accctgcccc catcccggga tgagctgacc aagaaccagg tcagcctgac ctgcctggtc | 1320 |
| aaaggcttct atcccagcga catcgccgtg gagtgggaga gcaatgggca accggagaac | 1380 |
| aactacaaga ccacgcctcc cgtgctggac tccgacggct ccttcttcct ctacagcaag | 1440 |
| ctcaccgtgg acaagagcag gtggcagcag gggaacgtct tctcatgctc cgtgatgcat | 1500 |
| gaggctctgc acaaccacta cacgcagaag agcctctccc tgtctccggg taaaaaagat | 1560 |
| cccaaatttt gggtgctggt ggtggttggt ggagtcctgg cttgctatag cttgctagta | 1620 |
| acagtggcct ttattatttt ttgggtgagg agtaagagga gcaggctcct gcacagtgac | 1680 |
| tacatgaaca tgactccccg ccgcccgg cccacccgca agcattacca gccctatgcc | 1740 |
| ccaccacgcg acttcgcagc ctatcgctcc aaacggggca gaaagaaact cctgtatata | 1800 |
| ttcaaacaac catttatgag accagtacaa actactcaag aggaagatgg ctgtagctgc | 1860 |
| cgatttccag aagaagaaga aggaggatgt gaactgagag tgaagttcag caggagcgca | 1920 |
| gacgcccccg cgtaccagca gggccagaac cagctctata cgagctcaa tctaggacga | 1980 |
| agagaggagt acgatgtttt ggacaagaga cgtggccggg accctgagat gggggggaaag | 2040 |
| ccgagaagga agaaccctca ggaaggcctg tacaatgaac tgcagaaaga taagatggcg | 2100 |
| gaggcctaca gtgagattgg gatgaaaggc gagcgccgga ggggcaaggg gcacgatggc | 2160 |
| ctttaccagg gtctcagtac agccaccaag gacacctacg acgcccttca catgcaggcc | 2220 |
| ctgcccccte gccagtgtac taattatgct ctcttgaaat tggctggaga tgttgagagc | 2280 |
| aatcccgggc catgcggat cagcaagccc cacctgcgga gcatcagcat ccagtgctac | 2340 |
| ctgtgcctgc tgctgaacag ccacttcctg accgaggccg gcatccacgt gttcatcctg | 2400 |
| ggctgcttca gcgccggact gcccaagacc gaggccaact gggtgaacgt gatcagcgac | 2460 |
| ctgaagaaga tcgaggacct gatccagagc atgcacatcg acgccaccct gtacaccgag | 2520 |
| agcgacgtgc accccagctg caaggtgacc gccatgaagt gctttctgct ggaactgcag | 2580 |
| gtgatcagcc tggaaagcgg cgacgccagc atccacgaca ccgtggagaa cctgatcatc | 2640 |
| ctggccaaca cagcctgag cagcaacggc aacgtgaccg agagcggctg caaagagtgc | 2700 |
| gaggaactgg aagagaagaa catcaaagag tttctgcaga gcttcgtgca catcgtgcag | 2760 |
| atgttcatca acaccagctg a | 2781 |

<210> SEQ ID NO 9
<211> LENGTH: 60
<212> TYPE: DNA
<213> ORGANISM: Artificial Sequence
<220> FEATURE:
<223> OTHER INFORMATION: SARS-CoV-2 S forward primer

<400> SEQUENCE: 9
tctagagatt acaaggatga cgacgataag taactcgaga tcgatccgga ttagtccaat    60

<210> SEQ ID NO 10
<211> LENGTH: 29
<212> TYPE: DNA
<213> ORGANISM: Artificial Sequence
<220> FEATURE:
<223> OTHER INFORMATION: SARS-CoV-2 S reverse primer

<400> SEQUENCE: 10
gtcgacgcac tggacacctt ttaaaatag                                      29

<210> SEQ ID NO 11
<211> LENGTH: 51
<212> TYPE: DNA
<213> ORGANISM: Artificial Sequence
<220> FEATURE:
<223> OTHER INFORMATION: pSFG_SARS-CoV2-Sdelta _Forward primer

<400> SEQUENCE: 11
tcatgcggca gctgttgctc tagagattac aaggatgacg acgataagta a 51

<210> SEQ ID NO 12
<211> LENGTH: 48
<212> TYPE: DNA
<213> ORGANISM: Artificial Sequence
<220> FEATURE:
<223> OTHER INFORMATION: pSFG_SARS-CoV2-Sdelta_Reverse primer

<400> SEQUENCE: 12
caccaagaac acaaacatgt cgacgcactg gacacctttt aaaatagc 48

<210> SEQ ID NO 13
<211> LENGTH: 48
<212> TYPE: DNA
<213> ORGANISM: Artificial Sequence
<220> FEATURE:
<223> OTHER INFORMATION: pLV_ SARS-CoV-2 Sdelta_Forward primer

<400> SEQUENCE: 13
ggtgtccagt gcgtcgacat gtttgtgttc ttggtgttgc ttccactg 48

<210> SEQ ID NO 14
<211> LENGTH: 40
<212> TYPE: DNA
<213> ORGANISM: Artificial Sequence
<220> FEATURE:
<223> OTHER INFORMATION: pLV_SARS-CoV-2 Sdelta_Reverse primer

<400> SEQUENCE: 14
atccttgtaa tctctagagc aacagctgcc gcatgagcag 40

<210> SEQ ID NO 15
<211> LENGTH: 51
<212> TYPE: DNA
<213> ORGANISM: Artificial Sequence
<220> FEATURE:
<223> OTHER INFORMATION: pSFG_ SARS-CoV2-S delta+_Forward primer -continued

<400> SEQUENCE: 15
tcctgcggca gctgctgctc tagagattac aaggatgacg acgataagta a            51

<210> SEQ ID NO 16
<211> LENGTH: 48
<212> TYPE: DNA
<213> ORGANISM: Artificial Sequence
<220> FEATURE:
<223> OTHER INFORMATION: pSFG_SARS-CoV-2 Sdelta+_Reverse primer

<400> SEQUENCE: 16
gaccaggaag acaaacatgt cgacgcactg gacacctttt aaaatagc                48

<210> SEQ ID NO 17
<211> LENGTH: 43
<212> TYPE: DNA
<213> ORGANISM: Artificial Sequence
<220> FEATURE:
<223> OTHER INFORMATION: pCAG_ SARS-CoV2-S delta+_Forward primer

<400> SEQUENCE: 17
ggtgtccagt gcgtcgacat gtttgtcttc ctggtcctgc tgc                     43

<210> SEQ ID NO 18
<211> LENGTH: 40
<212> TYPE: DNA
<213> ORGANISM: Artificial Sequence
<220> FEATURE:
<223> OTHER INFORMATION: pCAG_SARS-CoV-2 Sdelta+_Reverse

<400> SEQUENCE: 18
atccttgtaa tctctagagc agcagctgcc gcaggagcag                         40

<210> SEQ ID NO 19
<211> LENGTH: 51
<212> TYPE: DNA
<213> ORGANISM: Artificial Sequence
<220> FEATURE:
<223> OTHER INFORMATION: pSFG_SARS-CoV-2 Smu_Forward primer

<400> SEQUENCE: 19
tcctgcggca gctgctgctc tagagattac aaggatgacg acgataagta a            51

<210> SEQ ID NO 20
<211> LENGTH: 48
<212> TYPE: DNA
<213> ORGANISM: Artificial Sequence
<220> FEATURE:
<223> OTHER INFORMATION: pSFG_SARS-CoV-2 Smu_Reverse primer

<400> SEQUENCE: 20
gaccaggaag acaaacatgt cgacgcactg gacacctttt aaaatagc                48

<210> SEQ ID NO 21
<211> LENGTH: 43
<212> TYPE: DNA
<213> ORGANISM: Artificial Sequence
<220> FEATURE:
<223> OTHER INFORMATION: pCAG_ SARS-CoV-2 Smu_Forward primer

<400> SEQUENCE: 21
ggtgtccagt gcgtcgacat gtttgtcttc ctggtcctgc tgc                     43

<210> SEQ ID NO 22

-continued

```
<211> LENGTH: 40
<212> TYPE: DNA
<213> ORGANISM: Artificial Sequence
<220> FEATURE:
<223> OTHER INFORMATION: pCAG_ SARS-CoV-2 Smu_Reverse primer

<400> SEQUENCE: 22
atccttgtaa tctctagagc agcagctgcc gcaggagcag                    40
```